United States Patent [19]

Krespan

[11] 4,275,225
[45] Jun. 23, 1981

[54] POLYFLUOROALLYLOXY COMPOUNDS, THEIR PREPARATION AND COPOLYMERS THEREFROM

[75] Inventor: Carl G. Krespan, Wilmington, Del.

[73] Assignee: E. I. Du Pont de Nemours and Company, Wilmington, Del.

[21] Appl. No.: 145,756

[22] Filed: May 1, 1980

Related U.S. Application Data

[63] Continuation-in-part of Ser. No. 20,354, Mar. 14, 1979, abandoned, which is a continuation-in-part of Ser. No. 850,729, Nov. 11, 1977, abandoned, which is a continuation-in-part of Ser. No. 747,029, Dec. 2, 1976, abandoned.

[51] Int. Cl.$^3$ .................. C07C 69/734; C07C 59/58
[52] U.S. Cl. .................. 560/174; 526/240; 526/243; 526/244; 526/245; 526/247; 526/248; 526/249; 526/250; 560/181; 560/183; 562/577; 562/582; 562/583; 562/586; 568/674; 568/684; 568/685
[58] Field of Search .............. 560/174, 181, 183; 562/577, 582, 583, 586

[56] References Cited

U.S. PATENT DOCUMENTS

| | | | |
|---|---|---|---|
| 2,671,799 | 3/1954 | Miller | 260/465.7 |
| 2,856,435 | 10/1958 | Lo | 260/614 |
| 3,114,778 | 12/1963 | Fritz et al. | 562/582 X |
| 3,180,895 | 4/1965 | Harris, Jr. et al. | 562/586 X |
| 3,321,532 | 5/1967 | Lorenz | 260/614 |
| 3,450,684 | 6/1969 | Darby | 260/87.5 |
| 3,467,638 | 9/1969 | Pattison | 260/87.5 |
| 3,527,742 | 9/1970 | Pittman et al. | 260/89.5 |
| 3,557,165 | 1/1971 | Dorfman et al. | 260/404 |
| 3,641,104 | 2/1972 | Anderson | 562/586 X |
| 3,674,820 | 7/1972 | Pittman et al. | 260/611 R X |
| 3,795,684 | 3/1974 | Domba | 260/343.9 |
| 3,799,992 | 3/1974 | Pittman et al. | 260/614 F |
| 4,131,740 | 12/1978 | England | 560/180 |
| 4,138,426 | 2/1979 | England | 260/465.6 |
| 4,153,804 | 5/1979 | Yamabe et al. | 560/183 |

OTHER PUBLICATIONS

Flory; "Principles of Polymer Chemistry", (1953), Cornell University Press, N.Y., pp. 172–174.
Yocum, et al.; "Functional Monomers", vol. 1, pp. 384–387, (1973), Marcel Dekker, Inc., N.Y.
Laible, Chem. Reviews, 58, pp. 807–816, (1958).
Repwood, et al., Canadian Journal of Chemistry, (1967), 45, pp. 389–395.
Young, Fluorine Chemistry Reviews, (1967), 1, pp. 386–397.
Kobrina, Fluorine Chemistry Reviews, (1974), 7, pp. 21–23 and 65–68.

Primary Examiner—Joseph P. Brust

[57] ABSTRACT

The reaction of a polyfluorocarbonyl compound such as a polyfluoroketone or polyfluorocarboxylic acid fluoride with fluoride ion and a polyfluoroallyl chloride, bromide or fluorosulfate produces a polyfluoroallyloxy carboxylic acid or ester, e.g., $CF_2=CFCF_2OCF_2CF_2COOH$. The polyfluoroallyloxy compounds copolymerize with ethylenically unsaturated monomers such as tetrafluoroethylene, chlorotrifluoroethylene or vinylidene fluoride to form polymers which are moldable, and in some cases electrically conducting or are water-wettable and dyeable.

7 Claims, No Drawings

POLYFLUOROALLYLOXY COMPOUNDS, THEIR PREPARATION AND COPOLYMERS THEREFROM

CROSS-REFERENCE TO RELATED APPLICATIONS

This application is a continuation-in-part of application Ser. No. 020,354, filed Mar. 14, 1979, now abandoned, which in turn is a continuation-in-part of application Ser. No. 850,729, filed Nov. 11, 1977, now abandoned, which is in turn a continuation-in-part of application Ser. No. 747,029, filed Dec. 2, 1976 by Carl George Krespan, now abandoned.

BACKGROUND OF THE INVENTION

1. Field of the Invention

This invention relates to polyfluoroallyloxy compounds, processes for their preparation and copolymers prepared therefrom.

2. Relation to the Prior Art

1. U.S. Pat. No. 2,856,435 to E. S. Lo discloses the preparation of perfluoroallyloxy-1,1-dihydroperfluoroalkanes from 3-chloropentafluoropropene and a 1,1-dihydroperfluoroalkanol in alkaline medium, e.g.

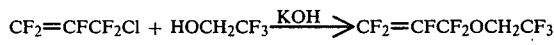

2. U.S. Pat. No. 2,671,799 to W. T. Miller discloses a process for replacing the chlorine in perfluoroallyl chloride (3-chloropentafluoropropene) with methoxy, cyano, iodo and nitrate groups, e.g.

3. M. E. Redwood and C. J. Willis, *Canad. J. Chem.*, 45, 389 (1967) describe the reaction of allyl bromide with cesium heptafluoro-2-propoxide to form 2-allyloxyheptafluoropropane:

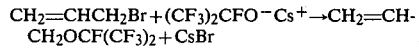

4. J. A. Young, *Fluorine Chemistry Reviews*, 1, 389-393 (1967) surveys the formation of perfluoroalkoxide anions by the action of alkali metal fluorides on perfluoroketones, perfluoroalkyloxiranes, perfluorocarboxylic acid fluorides and perfluoroalkyl fluorosulfates. References 5-9 which follow are examples of the nucleophilic reactions of perfluoroalkoxide anions.

5. U.S. Pat. No. 3,450,684 to R. A. Darby discloses the preparation of fluorocarbon polyethers and their polymers by reaction of perfluoroalkanoyl fluorides with potassium or quaternary ammonium fluoride and hexafluoropropene epoxide.

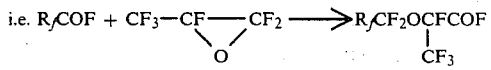

6. U.S. Pat. No. 3,674,820 to A. G. Pittman and W. L. Wasley discloses the reaction of fluoroketones with an alkali metal fluoride and an omega-haloalkanoic acid ester to form an omega-(perfluoroalkoxy) alkanoic acid ester, e.g.

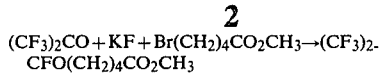

7. U.S. Pat. No. 3,795,684 to E. Domba also discloses the reaction of hexafluoroacetone with potassium fluoride and an omega-haloalkanoic acid ester.

8. U.S. Pat. No. 3,527,742 to A. G. Pittman and W. L. Wasley, discloses the reduction of the compounds of Reference 6 to the corresponding alcohols and their esterification to polymerizable acrylates.

9. U.S. Pat. No. 3,799,992 to A. G. Pittman and W. L. Wasley discloses the preparation of (perfluoroalkoxy)-vinyl compounds by reaction of a perfluoroketone with an alkali metal fluoride and a 1,2-dihaloethane, followed by dehydrohalogenation of the intermediate 2-perfluoroalkoxyhaloethane.

e.g. $(CF_3)_2CO + KF + BrCH_2CH_2Br \longrightarrow$ $(CF_3)_2CFOCH_2CH_2Br \xrightarrow{-HBr} (CF_3)_2CFOCH=CH_2$ 10. U.S. Pat. No. 3,321,532 to C. E. Lorenz discloses the rearrangement of perfluoro-2-alkoxyalkanoyl fluorides to perfluoroalkoxyolefins by passage over a metal oxide at 100°-400° C., e.g.,

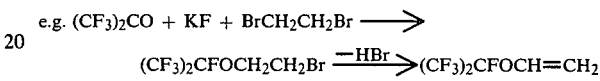

11. U.S. Pat. No. 3,467,638 to D. B. Pattison discloses polyfluorovinyl ethers of the formula

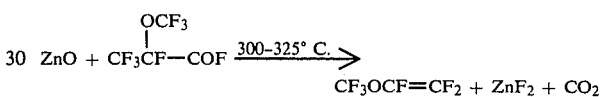

where n is 1 or 2 and copolymers containing said ethers.

12. L. S. Kobrina, Fluorine Chemistry Reviews, vol, 7, p. 67, Marcel Dekker, Inc., N.Y. (1974), discloses the substitution of hydroxyl into $-OC_6F_5$ groups to form $-OC_6F_4OH$.

13. U.S. Pat. No. 4,131,740 to D. C. England discloses the compound $ROOC-CF_2-COF$, hexafluoropropene oxide adducts with the formula

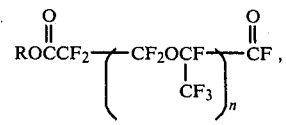

vinyl ethers prepared from same, of the formula

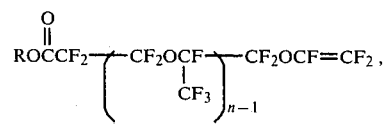

and copolymers prepared from said vinyl ethers; n is 1 to 6, and R is $CH_3$ or $C_2H_5$.

14. U.S. Pat. No. 4,138,426 to D. C. England discloses the nitrile

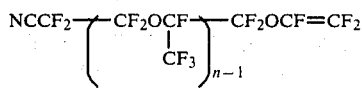

where n is 1 to 6.

SUMMARY OF THE INVENTION

According to the present invention there is provided a polyfluoroallyloxy compound having the formula $$CF_2=CCF_2OR_F$$
$$\phantom{CF_2=C}|$$
$$\phantom{CF_2=CCF_2OR}X$$

wherein X is —Cl or —F, and $R_F$ is:

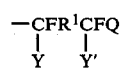  (i)

wherein $R^1$ is a carbon-carbon bond or a linear or branched perfluoroalkylene group of 1 to 12 carbon atoms; Q is —$SO_2F$, —COF, —F, —Cl, —Br, —I, —CN, —$CO_2H$, —$OCF_2CF=CF_2$, —$OC_6F_5$, or —$CO_2R^4$ where $R^4$ is —$CH_3$ or —$C_2H_5$; Y and Y', independently, are —F or —$CF_3$ and only Y or Y' can be —$CF_3$; or $$—CF(R^2)_2 \qquad \text{(ii)}$$

wherein $R^2$ is —F, —$CF_2Cl$, —$CF_2CN$, —$CF_2COF$, —$CF_2CO_2H$, —$CF_2OCF(CF_3)_2$ or —$CF_2CO_2R^4$ where $R^4$ is defined as above; or

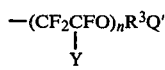  (iii)

wherein $R^3$ is a linear or branched perfluoroalkylene group of carbon content such that the moiety

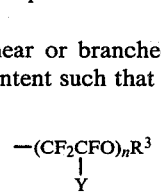

does not exceed 15 carbon atoms; Y is —F or —$CF_3$; n is 1 to 4; and Q' is defined as for Q above; or

  (iv)

wherein G is —COF, —$CO_2H$ or —$CO_2R^4$ where $R^4$ is —$CH_3$ or —$C_2H_5$.

There is also provided a process for preparing a polyfluoroallyloxy compound which comprises:
(1) mixing and reacting
(a) a carbonyl compound having the formula:

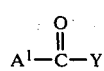

wherein $A^1$ is

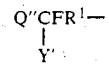

where $R^1$ is a carbon-carbon bond or a linear or branched perfluoroalkylene group of 1 to 12 carbon atoms; Q" is —$SO_2F$, —$SO_2OCF_2CH_3$, —$OCF_2CF=CF_2$, —COF, —F, —Cl, —Br, —I, —CN, —$OC_6F_5$ or —$CO_2R^4$ is —$CH_3$ or —$C_2H_5$; Y and Y', independently, are —F or —$CF_3$ and only Y or Y' can be —$CF_3$; or
(b) a carbonyl compound having the formula:

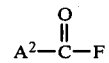

wherein $A^2$ is

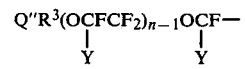

where $R^3$ is a linear or branched perfluoroalkylene group of carbon content such that the moiety

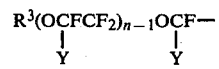

does not exceed 14 carbon atoms; Y is —F or —$CF_3$; n is 1 to 4; and Q" is defined as above; or
(c) a carbonyl compound having the formula:

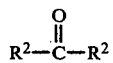

wherein $R^2$ is —F, —$CF_2Cl$, —$CF_2CN$, —$CF_2COF$, —$CF_2CO_2H$, —$CF_2OCF(CF_3)_2$ or —$CF_2CO_2R^4$ where $R^4$ is —$CH_3$ or —$C_2H_5$,
with a metal fluoride of the formula MF where M is K—, Rb—, Cs—, or $R_4N$—where each —R, alike or different, is alkyl of 1 to 6 carbon atoms; and
(2) mixing the mixture from (1) with a perfluoroallyl compound of the formula

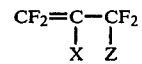

wherein
X is —Cl or —F; and
Z is —Cl, —Br or —$OSO_2F$.

Also provided is a copolymer of the aforesaid polyfluoroallyloxy compound with at least one ethylenically unsaturated monomer.

DETAILS OF THE INVENTION

This invention relates to compounds of formulae 4, 7, 9, and 10, prepared from starting materials 1, 2 and either 3, 6, 8, or 8' according to the following equations:

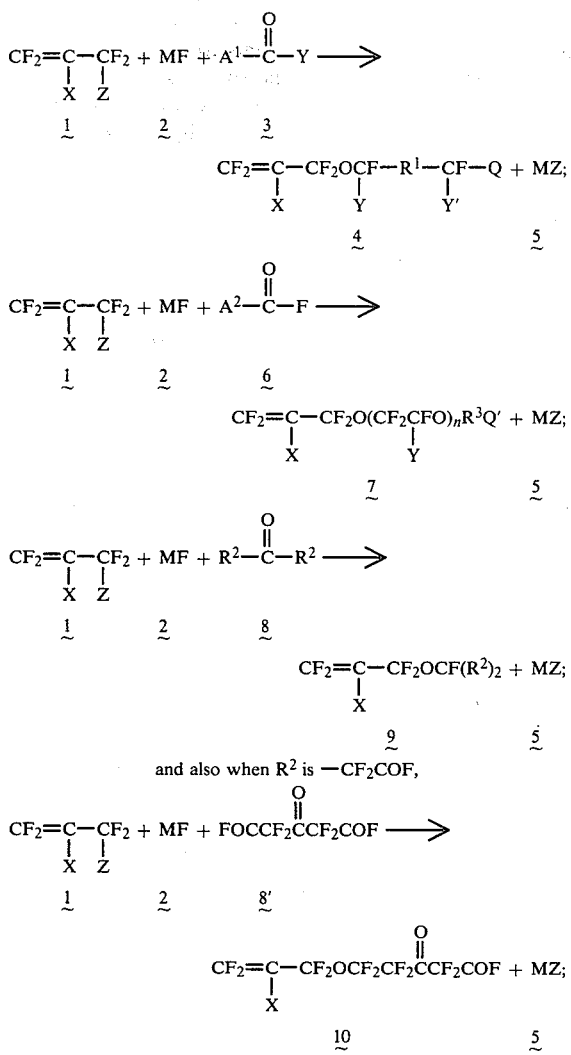

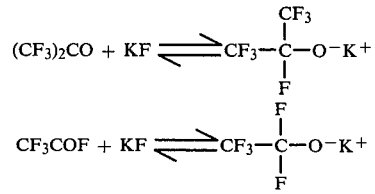

the terminal —COF group in 10 being convertible to the groups —CO$_2$H and —CO$_2$R$^4$ where R$^4$ is —CH$_3$ or —C$_2$H$_5$.

In the above equations, starting materials 1, 2, and either 3, 6, 8, or 8' react to give products 4, 7, 9, or 10, respectively, and a metal salt 5. The symbols A, R$^1$, R$^2$, R$^3$, M, n, Q, Q', X, Y, Y' and Z are as given in the Summary. Products represented by general structures 4, 7, 9, and 10 can be converted into useful copolymers especially with tetrafluoroethylene, vinylidene fluoride, chlorotrifluoroethylene and provided tetrafluoroethylene or vinylidene fluoride is also present perfluoro(-methyl vinyl ether), perfluoro(propyl vinyl ether), and hexafluoropropylene.

Preferred polyfluoroallyloxy compounds of formula 4 are those in which R$^1$ is a carbon-carbon bond or a linear or branched perfluoroalkyl group of 1 to 12 carbon atoms and Q is —SO$_2$F, —COF, —F, —Cl, —Br, —CN, —OC$_6$F$_5$, —OCF$_2$CF=CF$_2$, —CO$_2$H and —CO$_2$R$^4$ where R$^4$ is —CH$_3$ or —C$_2$H$_5$; and X is —F.

Especially preferred polyfluoroallyloxy compounds of formula 4 are those in which R$^1$ is a carbon-carbon bond or linear perfluoroalkyl and Q is —SO$_2$F, —COF, —CN or —CO$_2$R$^4$; and X is —F.

Preferred polyfluoroallyloxy compounds of formula 7 are those in which R$^3$ is linear; Q' is —SO$_2$F, —COF, —CN or —CO$_2$R$^4$; and X is —F.

Preferred polyfluoroallyloxy compounds of formula 9 are those in which R$^2$ is —CF$_2$COF, —CF$_2$CN, or —CF$_2$CO$_2$R$^4$; and X is —F.

The polyfluoroallyl group of the products 4, 7, 9 and 10 is derived from the corresponding polyfluoroallyl chloride, bromide or fluorosulfate 1 by nucleophilic displacement of the chloride, bromide or fluorosulfate group with a preformed polyfluoroalkoxide anion derived from the metal fluoride 2 and the carbonyl compound 3, 6, or 8. The synthesis is thus a one-vessel sequential addition of reagents, 3, 6 or 8 and 1 to a suspension or solution of 2 in a suitable solvent.

Polyfluoroallyl fluorosulfates are the preferred reagents for this displacement, and they can be prepared conveniently by treatment of polyfluoroalkenes with sulfur trioxide, as described in coassigned application Ser. No. 718,337, filed Aug. 27, 1976, in the name of D. C. England, now abandoned. Such reactions are typically carried out in sealed Carius tubes at temperatures of 25°–90° C. for periods of 16 hours to 4 days, and the product fluorosulfates are purified by fractional distillation. A preparation of the preferred perfluoroallyl fluorosulfate (pentafluoro-2-propenyl fluorosulfate) is given in Example 2.

Stable metal polyfluoroalkoxides are formed by the reaction of certain metal fluorides with polyfluorinated ketones and acid fluorides (J. A. Young, loc. cit.), thus:

The usefulness of such intermediate polyfluoroalkoxides is determined by their stability, as measured by their ease of thermal decomposition. Because their formation is reversible, the equilibrium concentrations of various species in a given reaction mixture are important quantities which determine whether or not the subsequent displacement will occur to form product 4, 7, 9, or 10. Solutions in which the equilibrium lies towards the right (high concentration of anion) will be more effective than those in which it lies towards the left (high concentration of carbonyl compound).

Polyfluoroalkoxide anion formation and chemistry is dependent upon the following four conditions, discussed in further detail by J. A. Young, loc. cit., F. W. Evans, M. H. Litt, A. M. Weidler-Kubanek and F. P. Avonda, J. Org. Chem., 33, 1837, 1839 (1968), and M. A. Redwood and C. J. Willis, Canad. J. Chem., 45, 389 (1967). (1) Stable polyfluoroalkoxide anions are formed when the carbonyl compound is highly fluorinated because the electron-withdrawing effect of the fluorine atoms distributes the negative charge over the entire anion. Substitution of some of the fluorine by chlorine, other fluoroalkyl groups or hydrogen destablizes the anion because these groups are less electron-withdrawing and the negative charge is not as readily accommodated. (2) Large cations such as K$^+$, Rb$^+$, Cs$^+$ and R$_4$N$^+$ favor the formation of stable polyfluoroalkoxides more than small cations such as Li⁺ and Na⁺ because the lattice energy of metallic fluorides is inversely proportional to cation size. In other words, large cation size and small lattice energy favors disruption of the metallic fluoride crystal structure to form the anion. (3) Solvents which have a high heat of solution for the polyfluoroalkoxide favor its formation. Aprotic polar solvents such as N,N-dimethylformamide (DMF), acetonitrile, and 1,2-dimethoxyethane (glyme) are very effective for this purpose. (4) When there are fluorine atoms alpha to the oxygen atom in the anion, loss of fluoride ion may compete with the desired reactions, e.g.,

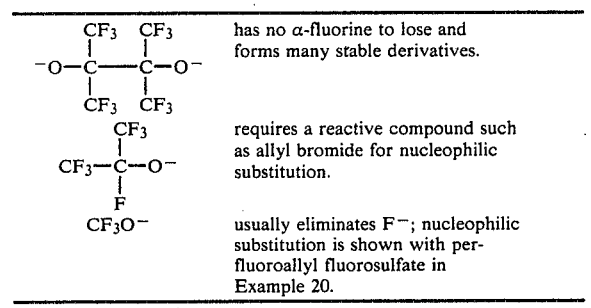

| | |
|---|---|
| | has no α-fluorine to lose and forms many stable derivatives. |
| | requires a reactive compound such as allyl bromide for nucleophilic substitution. |
| CF₃O⁻ | usually eliminates F⁻; nucleophilic substitution is shown with perfluoroallyl fluorosulfate in Example 20. |

In the practice of this invention, the polyfluoroalkoxide anion is preferably preformed by the addition of the carbonyl compound to a stirred mixture of the metal fluoride in a suitable aprotic solvent. The completeness of formation of the anion is generally signalled by the extent to which the metal fluoride dissolves in the solvent as the reaction progresses. The stoichiometry of polyfluoroalkoxide anion formation requires one molar equivalent of metal fluoride for each carbonyl group which is converted to its anion, e.g.:

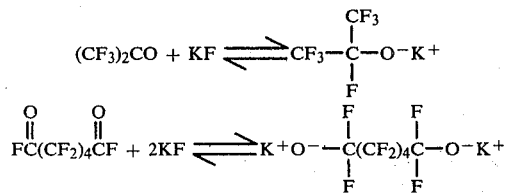

The presence of up to a twice-molar excess of metal fluoride is generally not detrimental. Two side effects of excess metal fluoride are: (1) to hinder the observation of the reaction endpoint because of the presence of undissolved solid in the reaction mixture, and (2) excess fluoride ion in solution may react directly with perfluoroallyl fluorosulfate to form hexafluoropropene.

Because of the limited thermal stability of polyfluoroalkoxides, their formation is usually accomplished between −20° C. and +60° C., preferably with external cooling to maintain the temperature between 0° C. and 10° C.

The time required to complete polyfluoroalkoxide formation varies with the carbonyl component, but it is preferably from 0.5 to 2 hours, each individual case being usually determined by how long it takes the reaction mixture to become homogeneous.

N,N-Dimethylformamide (DMF), acetonitrile, N,N-dimethylacetamide (DMAC), γ-butyrolactone, 1,2-dimethoxyethane (glyme), 1-(2-methoxyethoxy)-2-methoxyethane (diglyme), 2,5,8,11-tetraoxadodecane (triglyme), dioxane, sulfolane, nitrobenzene and benzonitrile are suitable, illustrative aprotic polar solvents for the preparation of polyfluoroalkoxides and their subsequent reaction with the polyfluoroallyl chloride, bromide or fluorosulfate. DMF, diglyme, triglyme and acetonitrile are preferred solvents for these reactions.

The apparatus, reactants and solvents should be adequately dried for use in the process of the invention because the presence of water hydrolyzes polyfluoroalkoxides:

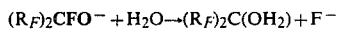

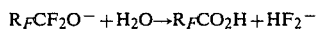

Metal fluorides which are useful in this invention are potassium fluoride (KF), rubidium fluoride (RbF), cesium fluoride (CsF) and tetraalkylammonium fluorides (R₄NF) such as tetraethylammonium fluoride ((C₂H₅)₄NF) and tetrabutylammonium fluoride (C₄H₉)₄NF). R, alike or different, is alkyl of 1 to 6 carbon atoms, preferably 1 to 4 carbon atoms. Potassium fluoride is preferred because of its availability, economic advantage, and ease of handling.

Polyfluorinated carbonyl compounds which are useful in this invention are ketones and carboxylic acid fluorides. Ketones give branched fluorocarbon products, whereas acid fluorides give primary fluorocarbon products in which the new ether linkage is at the primary or secondary center:

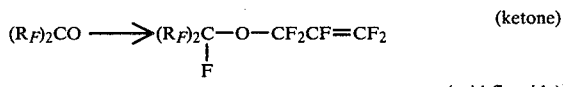

Polyfluorinated ketones which are useful include hexafluoroacetone, chloropentafluoroacetone, 1,3-dichlorotetrafluoroacetone, 1,1-difluoroethyl 2-oxopentafluoropropanesulfonate, dimethyltetrafluoroacetone-1,3-dicarboxylate, 1,3-bis(2-heptafluoropropoxy)tetrafluoropropanone, octafluorobutanone, decafluoro-2-pentanone, dodecafluoro-2-hexanone, tetradecafluoro-2-heptanone, hexadecafluoro-2-octanone, octadecafluoro-2-nonanone, eicosafluoro-2-decanone, and 3-ketotetrafluoroglutaroyl fluoride.

Polyfluorinated acid fluorides which are useful include carbonyl fluoride, trifluoroacetyl fluoride, pentafluoropropionyl fluoride, heptafluorobutyroyl fluoride, nonafluoropentanoyl fluoride

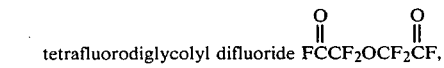

undecafluorohexanoyl fluoride, tridecafluoroheptanoyl fluoride, pentadecafluorooctanoyl fluoride, heptadecafluorononanoyl fluoride, nonadecafluorodecanoyl fluoride, difluoromalonyl difluoride, tetrafluorosuccinyl difluoride, hexafluoropropane-1,3-dioyl difluoride (hexafluoroglutaryl difluoride), octafluorobutane-1,4-dioyl difluoride (octafluorodipoyl difluoride), decafluoropentane-1,5-dioyl difluoride (decafluoropimelyl difluoride), dodecafluorohexane-1,6-dioyl difluoride (dodecafluorosuberyl difluoride), fluorosulfonyldifluoroacetyl fluoride, 2-(fluorosulfonyl)tetrafluoropropionyl fluoride, 2-(heptafluoropropoxy)tetrafluoropropionyl fluoride, 2-[2-(1-heptafluoropropoxy) hexafluoropropoxy]-tetrafluoropropionyl fluoride, 2-{2-[2-(1-heptafluoropropoxy)hexafluoropropoxy]hexafluoropropoxy}tetrafluoropropionyl fluoride,

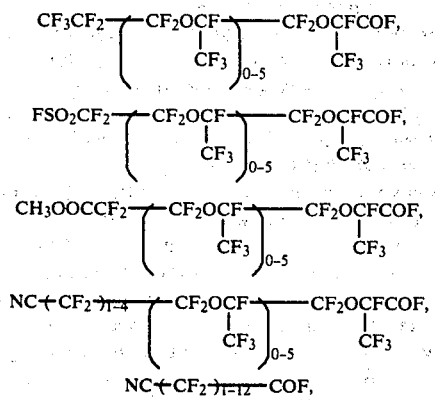

carbomethoxydifluoroacetyl fluoride, cyanodifluoroacetyl fluoride, 5-carbomethoxyperfluoro(2-methyl-3-oxavaleroyl)fluoride and 2-(pentafluorophenoxy)tetrafluoropropionyl fluoride.

The ketone 1,1-difluoroethyl 2-oxopentafluoropropanesulfonate (Example 3) is a special case as a starting material because it is an in situ source of 2-oxopentafluoropropanesulfonyl fluoride since the latter has not been isolated.

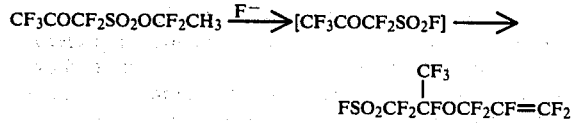

Many of the above starting materials are commercially available, e.g., PCR, Gainesville, Fla., is a supplier of fluorinated ketones and carboxylic acids. Examples 2, 3, 4, 5, 7, 10, 11, 12, 13, 16, 19, 23 and 24 give sources and methods of preparation of some compounds which are not commercially available. Generally, perfluoroketones can be prepared from the esters of perfluoroalkanecarboxylic acids and from the reaction of carbonyl fluoride with perfluoroalkenes (W. A. Sheppard and C. M. Sharts, "Organic Fluorine Chemistry", p. 365-368, W. A. Benjamin, New York, 1969, H. P. Braendlin and E. T. McBee, *Advances in Fluorine Chemistry*, 3, 1 (1963)). Perfluoroalkanecarboxylic acid fluorides and perfluoroalkane-α,ω-dicarboxylic acid difluorides are prepared by treatment of the corresponding acids with sulfur tetrafluoride, by the addition of carbonyl fluoride to perfluoroalkenes (F. S. Fawcett, C. W. Tullock and D. D. Coffman, *J. Amer. Chem. Soc.*, 84 4275, 4285 (1962)) and by electrolysis of alkanecarboxylic acids in hydrogen fluoride (M. Hudlický, "Chemistry of Fluorine Compounds", p. 86, MacMillan Co., New York, 1962). Perfluoroalkanedicarboxylic acids are prepared by oxidation of fluorinated α,ω-dialkenes or fluorinated cycloalkenes (Hudlický, loc. cit., p. 150-152). Perfluoroalkyl polyethers with a terminal acid fluoride group can be made from hexafluoropropene oxide and its fluoride ion induced oligomers, as described by R. A. Darby, U.S. Patent 3,450,684 (1969) and by P. Tarrant, C. G. Allison, K. P. Barthold and E. C. Stump, Jr., *Fluorine Chem. Rev.*, 5, 88 (1971).

The stoichiometry of the displacement with polyfluoroallyl chloride, bromide or fluorosulfate requires one molar equivalent of this reagent for each reactive center in the polyfluoroalkoxide anion. With a difunctional polyfluoroalkoxide, however, the stoichiometry can be adjusted to give either the mono- or the di-substitution product, thus:

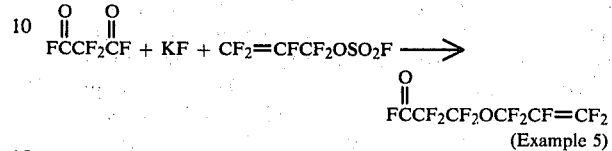
(Example 5)

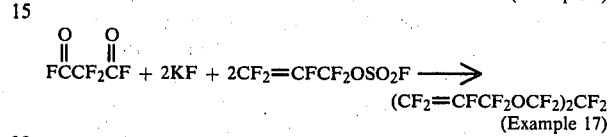
(Example 17)

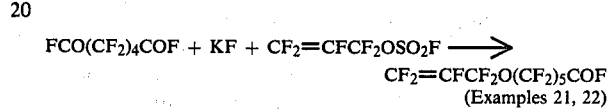
(Examples 21, 22)

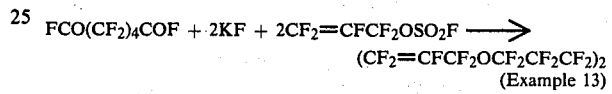
(Example 13)

The formation of the polyfluoroalkoxide and its subsequent reaction with the polyfluoroallyl chloride, bromide or fluorosulfate can be carried out sequentially without isolation of intermediates in glass apparatus at atmospheric pressure using the normal precautions to exclude moisture. The use of cooling baths and low temperature condensers (e.g. those packed with dry ice and acetone mixtures) serves to moderate the reactions and facilitate the retention of volatile reagents and products. The progress of the displacement reaction is conveniently followed by the appearance of a precipitate of the salt MZ (5), by gas liquid partition chromatography (glpc) and by fluorine nuclear magnetic resonance spectroscopy ($^{19}F$ NMR).

The displacement reaction can be carried out between $-20°$ C. and $+80°$ C., and is preferably between $0°$ C. and $30°$ C. Typically, the reaction mixture is cooled externally at $0°$ C. to $15°$ C. during the addition of the polyfluoroallyl chloride, bromide or fluorosulfate, and is then allowed to warm up to $25°$ C. to $30°$ C. for the remainder of the reaction time.

The time required to complete the displacement reaction varies from one to 24 hours, and is preferably from 2 to 4 hours. Typically, the reaction mixture is externally cooled for 5 to 45 min while the polyfluoroallyl chloride, bromide or fluorosulfate is being added, and is then stirred at room temperature for 2 to 3 hours.

The products of the reaction are isolated by standard procedures. In some cases, the reaction product is appreciably more volatile than the high-boiling solvent used (diglyme bp $162°$ C., DMF bp $153°$ C.) and can be distilled into a trap cooled to $-80°$ C. by warming the reaction vessel to $30°$ C. to $50°$ C. under a reduced pressure of 1 to 200 mm of Hg. Alternatively, the reaction mixture can be poured into five to ten times its volume of water; the insoluble lower layer of fluorinated product is separated, washed free of solvent with more water, dried and fractionally distilled from phosphorus pentoxide or concentrated sulfuric acid.

The polyfluoroallyloxy compounds of this invention are unsaturated monomers which can be converted to new and useful polymers. Polyfluoroallyloxy monomers can be homopolymerized under high pressure to oligomeric compositions of matter. The economic factors of a costly monomer and the necessity for high pressure operation, however, make it preferable to incorporate these monomers into copolymers formed with less expensive ethylenically unsaturated monomers, e.g., olefins such as ethylene and halogenated olefins such as tetrafluoroethylene, trifluoroethylene, vinylidene fluoride, chlorotrifluoroethylene, and provided tetrafluoroethylene or vinylidene fluoride is also present perfluoro(methyl vinyl ether), perfluoro(propyl vinyl ether), and hexafluoropropylene. Halogenated olefins are preferred, especially tetrafluoroethylene, vinylidene fluoride, chlorotrifluoroethylene, and mixtures of tetrafluoroethylene with perfluoro(methyl vinyl ether), perfluoro(propyl vinyl ether) or hexafluoropropylene. Such copolymers have either more desirable or entirely new properties not possessed by e.g., poly(tetrafluoroethylene), poly(trifluoroethylene), poly(vinylidene fluoride), poly(chlorotrifluoroethylene) or polyethylene. Copolymerization may be defined as any process whereby two or more monomers are incorporated as integral parts of a high polymer. A copolymer is the product resulting from such a process. It is not necessary that the relative numbers of the different types of unit be the same in different molecules of the copolymer or even in different portions of a single molecule.

Copolymers which contain from about 5–55 weight percent (about 1–25 mole percent) of polyfluoroallyloxy comonomer have lower melting points than the corresponding polyfluoroolefins, and consequently are more readily molded and shaped into useful objects. Copolymers which contain from about 0.1–10 weight percent, preferably about 1–10 percent (about 0.3–5 mole percent) of a polyfluoroallyloxy comonomer with pendant $-SO_2F$ or $-COF$ groups can be partially hydrolyzed to a copolymer bearing $-SO_2OH$ or $-CO_2H$ groups which have an affinity for cationic dye molecules. Thus, it is possible to dye fluorocarbon polymers in a variety of colors. This cannot be done with polyfluoroolefins which do not have incorporated comonomer of this type. Copolymers which contain from about 5 to 35 weight percent (about 1.0 to 10 mole percent) of a polyfluoroallyloxy comonomer with pendant $-SO_2F$, $-OC_6F_5$, or $-COF$ groups can also be partially or essentially completely hydrolyzed to a copolymer bearing hydrophilic $-SO_2OH$, $-OC_6F_4OH$ and $-CO_2H$ groups. Such a copolymer has an affinity for water and is water-wettable. Polyfluoroolefins which do not have incorporated a comonomer of this type are not wetted and are impermeable to water. A second important feature of copolymers which contain about 1.0 to 10 mole percent of a polyfluoroallyloxy comonomer bearing $-SO_2OH$ or $-CO_2H$ groups or ionized forms thereof, e.g., $-SO_2O^-Na^+$ or $-CO_2^-Na^+$, is their capacity for ion exchange. A specific use for such polymers is in a chloroalkali cell, such as disclosed in German Patent Application No. 2,251,660, published April 26, 1973, and Netherlands Patent Application No. 72.17598, published June 29, 1973, wherein an ion-exchange polymer in the form of a film membrane or diaphragm is used to separate the anode and cathode portion of the cell from which chlorine and sodium hydroxide are respectively produced from brine flowing within the anode portion of the cell.

Copolymers which contain from about 0.1–10 weight percent of a polyfluoroallyloxy comonomer having pendant $-CN$ groups are useful for imparting cure sites in fluoroelastomer compositions.

The properties of each copolymer depend upon the distribution of monomer units along the polymer chain since a copolymer is not a physical mixture of two or more polymers each derived from the respective monomers but a new material incorporating each monomer. It is well known that the composition of such a copolymer may also be quite different from that of the monomer mixture (feed) from which it is formed. Furthermore, "the relative tendencies of monomers to be incorporated into polymer chains do not correspond at all to their relative rates of polymerization alone . . . the reactive properties of a growing polymer chain depend primarily upon the monomer unit at the growing end, and not upon the length and composition of the chain as a whole.", C. Walling, "Free Radicals In Solution", pages 99–100, John Wiley & Sons, Inc., New York (1957).

The copolymerization reaction to prepare the present copolymers can be carried out either in a nonaqueous or an aqueous medium with the reactants and initiator in solution, suspension, or emulsion form in a closed vessel with agitation. This type of reaction is well known to those skilled in the art.

The copolymerization is initiated by a free radical type initiator which is generally present at a concentration of from 0.001 to 5 percent by weight of the reaction mixture, and is preferably from 0.01 to 1.0 percent by weight. Such free radical initiator systems are preferably operable at or below 25° C., and are exemplified by, but not restricted to pentafluoropropionyl peroxide $(C_2F_5COO)_2$, dinitrogen difluoride $(N_2F_2)$, azobisisobutyronitrile, ultraviolet irradiation and ammonium or potassium persulfate; mixtures of iron (II) sulfate with hydrogen peroxide, ammonium or potassium persulfate; cumene hydroperoxide, t-butyl hydroperoxide; mixtures of silver nitrate and ammonium or potassium persulfate; mixtures of trifluoroacetic acid, pentafluoropropionic acid, heptafluorobutyric acid or pentadecafluorooctanoic acid with ammonium or potassium persulfate. The peroxide systems may contain additionally sodium sulfite, sodium metabisulfite, or sodium thiosulfate.

When aqueous emulsion systems are used for copolymerization they contain emulsifying agents in the form of the sodium or potassium salts of saturated aliphatic acids of between about 14 and 20 carbon atoms or of perfluoroalkanoic acids and perfluoroalkanesulfonic acids of between 6 and 20 carbon atoms, e.g., potassium stearate or potassium pentadecafluorooctanoate. These emulsifiers may constitute between 0.1 and 10.0 weight percent of the reaction mixture and preferably constitute between 0.5 and 5 parts by weight percent.

Aqueous emulsion systems are customarily buffered to pH 7 or above by the addition of reagents such as disodium hydrogen phosphate, sodium metaborate, or ammonium metaborate to the amount of about 1 to 4 weight percent of the reaction mixture.

The following three types of copolymerization systems are preferred in preparing the preferred copolymers of this invention:

(1) Solutions of two or more comonomers in 1,1,2-trichloro-1,2,2-trifluoroethane (Freon ® 113) solvent containing pentafluoropropionyl peroxide are shaken in an autoclave at about 25° C. for about 20 hours. The crude polymer is isolated by evaporation of the solvent and freed from monomers and lower oligomers by washing with more solvent.

(2) An aqueous emulsion of two or more comonomers containing an emulsifier such as potassium perfluorooctanesulfonate and an initiator such as ammonium persulfate is shaken in an autoclave at about 700° C. and internal pressures of 30-200 p.s.i.g. for 0.75 to 8 hours. The polymer is isolated by filtration or centrifugation.

(3) The polyfluoroallyloxy comonomer may be used as the solvent in place of 1,1,2-trichloro-1,2,2-trifluoroethane in method (1) when it is desired to incorporate a large proportion (up to 25 mole percent) of the polyfluoroallyloxy component in the polymer.

SPECIFIC EMBODIMENTS OF THE INVENTION

The following illustrative examples demonstrate ways of carrying out the invention. All parts and percentages are by weight unless otherwise stated. For structure confirmation analyses, fluorine nuclear magnetic resonance chemical shifts are in parts per million from internal fluorotrichloromethane, and proton nuclear magnetic resonance chemical shifts are in parts per million from internal tetramethylsilane. Infrared and nuclear magnetic resonance spectra were recorded on undiluted liquid samples unless otherwise stated.

EXAMPLE 1

1-(Heptafluoro-2-propoxy)-1,1,3,3,-tetrafluoro-2-chloro-2-propene $$(CF_3)_2CO + KF + CF_2=CClCF_2Cl \rightarrow (CF_3)_2CFOCF_2CCl=CF_2$$

Hexafluoroacetone (16.6 g, 0.10 mol) was distilled into a stirred mixture of potassium fluoride (5.80 g, 0.10 mol) and 1-(2-methoxyethoxy)-2-methoxyethane (hereinafter referred to as diglyme) (100 ml) to give a homogeneous solution. This mixture was maintained at 25°-30° C. and treated with 1,2-dichloro-1,1,3,3,-tetrafluoropropene (18.3 g, 0.10 mol, prepared according to J. E. Bissey, H. Goldwhite and D. G. Rowsell, *J. Org. Chem.*, 32, 1542 (1967)). The mixture was stirred overnight and then it was poured into water (500 ml). The lower layer was washed with water (250 ml), dried, and distilled to give 1-(heptafluoro-2-propoxy)-1,1,3,3-tetrafluoro-2-chloropropene (13.0 g, 0.039 mol, 39%), bp 82°-83° C. whose structure was confirmed by the following: $\lambda_{max}$ 5.72 (CCl=CF$_2$) and 7.5-10 μm (CF, C-O); $^{19}$F NMR, −64.9 (m) 2F, −OCF$_2$C=C; −76.0 (2nd order m) 2F, C=CF$_2$; −81.2 (t J=5.7 Hz, each member d J=2.2 Hz) 6F, CF$_3$; and −146.7 ppm (t J=22.9 Hz each member septet J=2.2 Hz) 1F, CFO.

Anal. Calcd for C$_6$ClF$_{11}$O: C, 21.67; Cl, 10.66. Found: C, 21.43; Cl, 10.89.

EXAMPLE 2

1-(1,1,1,2,3,3-Hexafluoro-3-chloro-2-propoxy)-pentafluoro-2-propene

A. Pentafluoro-2-propenyl fluorosulfate (Perfluoroallyl fluorosulfate)

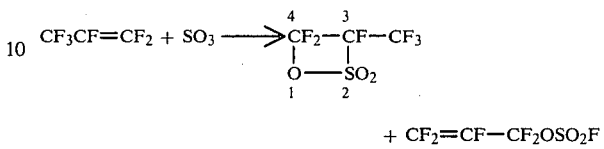

$$+ CF_2=CF-CF_2OSO_2F$$

A mixture of commercial liquid sulfur trioxide (10 ml) and hexafluoropropene (45 g, 0.30 mol) was sealed in a Carius tube at liquid nitrogen temperature, mixed well at 25° C., allowed to stand for 4 days at 25° C., and finally heated in a steam bath for 6 hours. From two such tubes, there was obtained by distillation, 3-(trifluoromethyl)-3,4,4-trifluoro-1-oxa-2-thiacyclobutane 2,2-dioxide (2-hydroxy-1-trifluoromethyl-1,2,2,-trifluoroethane sulfonic acid sultone, D. C. England, M. A. Dietrich and R. V. Lindsey, Jr., *J. Amer. Chem. Soc.*, 82 6181 (1960)) (25 g, 22%) bp 44° C., and pentafluoro-2-propenyl fluorosulfate (hereinafter referred to as perfluoroallyl fluorosulfate) (73 g, 63%), bp 58°-60° C.

Perfluoroallyl fluorosulfate is characterized by: $\lambda_{max}$ 5.55 (C=C) and 6.75 μm (SO$_2$); $^{19}$F NMR, 46.1 (t J=8.5 Hz, each member d J=1.8 Hz) 1F, SO$_2$F, −74.0 (d J=28.2 Hz, each member d J=13.9 Hz, d J=8.5 Hz, d J=7.8 Hz) 2F, −91.2 (d J=50 Hz, each member d J=40.5 Hz, t J=7.8 Hz) 1F, −104.7 (d J=119.4 Hz, each member d J=50 Hz, d J=28.2 Hz) 1F, and −192.4 ppm (d J=119.4 Hz, each member d J=40.5 Hz, t J=13.9 Hz, d J=1.8 Hz) 1F.

B. 1-(1,1,1,2,3,3-Hexafluoro-3-chloro-2-propoxy)-pentafluoro-2-propene $$CF_3COCF_2Cl + KF + CF_2=CFCF_2OSO_2F \longrightarrow$$

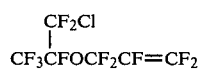

A suspension of potassium fluoride (5.80 g, 0.10 mol) and diglyme (100 ml) was stirred at 20° C. in a cooling bath while chloropentafluoroacetone (18.3 g, 0.10 mol) was distilled in. After the potassium fluoride had dissolved, perfluoroallyl fluorosulfate (23.0 g, 0.10 mol) was added rapidly with cooling of the reaction mixture. The resulting exothermic reaction was accompanied by the precipitation of solid. The mixture was stirred at 25° C. for one hour, and then the volatile components were transferred to a trap cooled to −80° C. by heating the reaction mixture at 42° C. (5 mm Hg). The volatile product was distilled from phosphorus pentoxide to give 1-(1,1,1,2,3,3-hexafluoro-3-chloro-2-propoxy)-pentafluoro-2-propene, (19.6 g, 0.059 mol, 59%) bp 85°-86° C. which was characterized by: $\lambda_{max}$ 5.55 (CF=CF$_2$) and 7-10 μm (CF, C—O); $^{19}$F NMR, −68.6 (m) 2F, CF$_2$Cl, −69.1 (m) 2F, CF$_2$O, −78.8 (m) 3F, CF$_3$, −93.2 (d J=54.7 Hz, each member d J=39.8 Hz, t J=7.5 Hz), 1F, cis-CF$_2$—CF=CF, −105.9 (d J=116.7 Hz, each member, d J=54.7 Hz, t J=24.0 Hz) 1F, trans—CF$_2$—CF=CF, −141.2 (t J=22.8 Hz, each member m) 1F, CF, and −190.4 ppm (d J=116.7 Hz, each member d J=39.8 Hz, t J=13.4 Hz) 1F, —CF$_2$CF̲=C.

Anal. Calcd for C$_6$ClF$_{11}$O: C, 21.67; Cl, 10.66. Found: C, 21.34; Cl, 10.21.

EXAMPLE 3

2-(1-Pentafluoro-2-propenyloxy)hexafluoropropane-1-sulfonyl fluoride
(2-Perfluoroallyloxypropane-1-sulfonyl fluoride)

A. 2-Oxopentafluoropropanesulfonic Acid

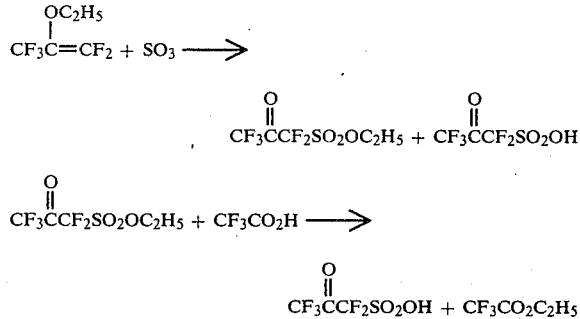

(i) Dropwise addition of sulfur trioxide (12.8 g, 0.16 mol) to 2-ethoxy-1,1,3,3,3-pentafluoropropene (D. W. Wiley and H. E. Simmons, *J. Org. Chem.*, 29, 1876 (1964)) (29.0 g, 0.165 mol) produced an exothermic reaction. The black reaction mixture was distilled to give recovered 2-ethoxy-1,1,3,3,3-pentafluoropropene (6.3 g, 0.036 mol, 22%, identified by ir) and ethyl 2-oxopentafluoropropanesulfonate (20.2 g, 0.078 mol, 49% conversion and 63% yield) bp 47°–48° C. (12 mm Hg): λ$_{max}$ 3.34 and 3.41 (saturated CH), 5.60 (C=O), 7.09 (SO$_2$O), and 7.6–8.5 μm (C—F, SO$_2$); $^1$H NMR, δ4.59 (q J=7.2 Hz) 2H, OCH$_2$ and 1.51 ppm (t J=7.2 Hz) 3H, CH$_3$; $^{19}$F NMR, −75.0 (t J=8.3 Hz) 3F, CF$_3$, and −107.4 ppm (q J=8.3 Hz) 2F, CF$_2$.

(ii) The above reaction was repeated at 0°–5° C. with sulfur trioxide (88 g, 1.1 mol) and 2-ethoxy-1,1,3,3,3-pentafluoropropene (176 g, 1.0 mol). The colorless reaction mixture, which darkened on standing overnight, was distilled to give recovered 2-ethoxy-1,1,3,3,3-pentafluoropropene (28.6 g, 0.16 mol, 16%) bp 46°–48° C., ethyl 2-oxopentafluoropropanesulfonate (145.1 g, 0.57 mol, 57% conversion and 68% yield) bp 48°–52° C. (12 mm Hg), and a higher boiling fraction composed mainly of 2-oxopentafluoropropanesulfonic acid. The crude acid was redistilled at 81°–82° C. (6.2 mm Hg), yield 35.6 g (0.16 mol, 16% conversion and 19% yield) of pure acid: λ$_{max}$ (CCl$_4$, CaF$_2$ plates) 3.3 and 4.2 (broad) (SOH), 5.58 (C=O), 7.13 (SO$_2$O) and 7.5–9 μm (CF, SO$_2$); $^1$H NMR δ10.2 ppm (s) SO$_2$OH; $^{19}$F NMR, −76.2 (t J=7.5 Hz) 3F, CF$_3$, and −108 ppm (q J=7.5 Hz) 2F, CF$_2$.

Anal. Calcd for C$_3$HF$_5$O$_4$S: C, 15.80; H, 0.44; F, 41.65; S, 14.06. Found: C, 15.95; H, 0.55; F, 41.55; S, 13.89.

(iii) Ethyl 2-oxopentafluoropropanesulfonate (25.6 g, 0.10 mol) was stirred at 25° C. and treated with trifluoroacetic acid (17.1 g, 0.15 mol). The mixture was allowed to stand overnight, and then it was heated to reflux (60° C.) in a spinning band still. Fractional distillation of the mixture at a pot temperature below 100° C. gave 2-oxopentafluoropropanesulfonic acid (18.4 g, 0.081 mol, 81%) bp 73° C. (2.6 mm Hg).

B. 1,1-Difluoroethyl 2-oxopentafluoropropanesulfonate

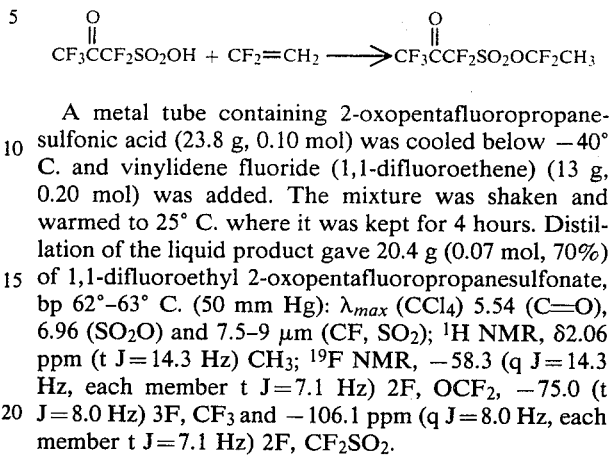

A metal tube containing 2-oxopentafluoropropanesulfonic acid (23.8 g, 0.10 mol) was cooled below −40° C. and vinylidene fluoride (1,1-difluoroethene) (13 g, 0.20 mol) was added. The mixture was shaken and warmed to 25° C. where it was kept for 4 hours. Distillation of the liquid product gave 20.4 g (0.07 mol, 70%) of 1,1-difluoroethyl 2-oxopentafluoropropanesulfonate, bp 62°–63° C. (50 mm Hg): λ$_{max}$ (CCl$_4$) 5.54 (C=O), 6.96 (SO$_2$O) and 7.5–9 μm (CF, SO$_2$); $^1$H NMR, δ2.06 ppm (t J=14.3 Hz) CH$_3$; $^{19}$F NMR, −58.3 (q J=14.3 Hz, each member t J=7.1 Hz) 2F, OCF$_2$, −75.0 (t J=8.0 Hz) 3F, CF$_3$ and −106.1 ppm (q J=8.0 Hz, each member t J=7.1 Hz) 2F, CF$_2$SO$_2$.

Anal. Calcd for C$_5$H$_3$F$_7$O$_4$S: C, 20.56; H, 1.03; F, 45.52. Found: C, 20.73; H, 1.03; F, 45.72.

A similar experiment on a 0.8-mol scale gave an 86% yield of product bp 60° C. (50 mm Hg). This material was stored in polytetrafluoroethylene bottles to avoid degradation.

C. 2-(1-Pentafluoro-2-propenyloxy)hexafluoropropane-1-sulfonyl fluoride

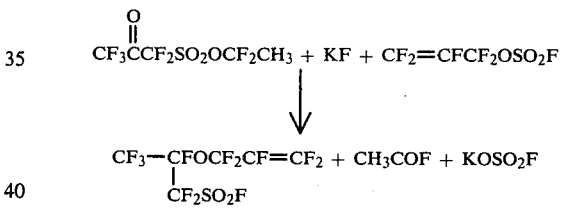

A suspension of dry potassium fluoride (5.80 g; 0.10 mol) in 2, 5, 8, 11-tetraoxadodecane (triglyme) (100 ml) was stirred and cooled at 0° C. while 1,1-difluoroethyl 2-oxopentafluoropropanesulfonate prepared as in Example 3B (29.2 g, 0.10 mol) was added. When the potassium fluoride had nearly all dissolved, perfluoroallyl fluorosulfate prepared as in Example 2A (23.0 g, 0.10 mol) was added at 0° C., and the resulting mixture was stirred at 20°–26° C. for 3 hours. Volatile components were removed by distillation at a flask temperature of 25° C. and 1 mm Hg pressure. The distillate was washed with cold dilute ammonium hydroxide, dried and distilled to give 2-(1-pentafluoro-2-propenyloxy)hexafluoropropane-1-sulfonyl fluoride (13.0 g, 0.034 mol, 34%), bp 47°–48° C. (60 mm Hg) whose structure was confirmed by: λ$_{max}$ 5.59 (CF=CF$_2$), 6.80 (SO$_2$F) and 7.5–10 μm (C—F, C—O, SO$_2$); $^{19}$F NMR, +45.4 (m) 1F, SO$_2$F, −70.0 (m) 2F, OCF$_2$, −78.0 (quintet J=10.7 Hz) 3F, CF$_3$, −91.5 (d J=51.5 Hz, each member d J=39.5 Hz, t J=7.5 Hz) 1F, cis-CF$_2$CF=CF̲, −104.8 (d J=117.0 Hz, each member d J=51.5 Hz, t J=25.5 Hz) 1F, trans-CF$_2$CF=CF̲, −107.0 and −108.4 (AB J=255 Hz, each member q J=10.7 Hz, m) 2F, CF̲$_2$SO$_2$F, −138.7 (t J=20.2 Hz, each member m) 1F, CF, and −190.8 ppm (d J=117.0 Hz, each member d J=39.5 Hz, t J=13.0 Hz) 1F, CF$_2$CF̲=C.

Anal. Calcd. for $C_6F_{12}O_3S$: C, 18.96; F, 59.98; S, 8.43. Found: C, 19.24; F, 60.06; S, 8.26.

In a similar reaction to Example 3C, it was shown by ir that the gases generated were composed mainly of acetyl fluoride and small amounts of hexafluoropropene and sulfuryl fluoride.

EXAMPLE 4

1-{1,3-bis(2-Heptafluoropropoxy)-2-pentafluoropropoxy}pentafluoro-2-propene

A. 1,3-bis(2-heptafluoropropoxy)tetrafluoropropanone

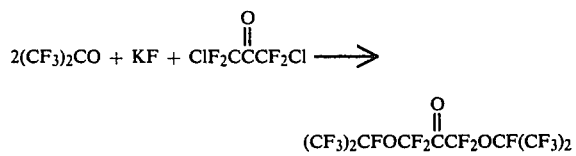

A mixture of dry potassium fluoride (21.0 g, 0.36 mol), dry N,N-dimethylformamide (DMF) (150 ml), hexafluoroacetone (59.8 g, 0.36 mol) and 1,3-dichlorotetrafluoroacetone (35.8 g, 0.18 mol) was heated at reflux (40°-60° C.) for 3 days. Distillation into a trap cooled to −80° C. gave recovered hexafluoroacetone (16.5 ml, 46%) and a 63 g of liquid bp 30°-145° C. The higher-boiling material was redistilled from sulfuric acid to give 1,3-bis(2-heptafluoropropoxy)tetrafluoropropanone (18.7 g, 0.037 mol, 21% conversion, 39% yield based on hexafluoroacetone), bp 117°-118° C.: $\lambda_{max}$ (CCl$_4$) 5.51 (C=O) and 7.5–9 $\mu$m (CF,C—O—C); MS m/e 479 (M-F)$^+$, 313 (M-F-CF$_3$COCF$_3$)$^+$, 263 (M-F-CF$_3$COCF$_3$-CF$_2$)$^+$, 235 [(CF$_3$)$_2$CFOCF$_2$]$^+$, 169 (C$_3$F$_7$)$^+$, 147 (CF$_3$COCF$_2$)$^+$, 97 (CF$_3$CO)$^+$ and 69 (CF$_3$)$^+$; $^{19}$F NMR, −75.0 (d J=21.5 Hz, each member septet J=5.5 Hz) 2F, OCF$_2$, −81.4 (m) 6F, CF$_3$, and −145.3 ppm (t J=21.5 Hz, each member septet J=2.1 Hz)1F, CF.

Anal. Calcd for $C_9F_{18}O_3$: C, 21.70; F, 68.66. Found: C, 21.60; F, 68.59.

B.
1-{1,3-bis(2-Heptafluoropropoxy)-2-pentafluoropropoxy}pentafluoro-2-propene

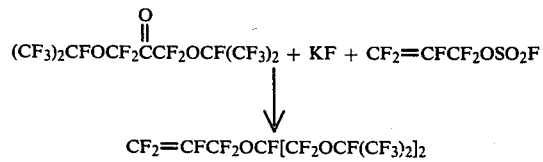

A mixture of 1,3-bis(2-heptafluoropropoxy)tetrafluoropropanone (20.0 g, 0.04 mol), diglyme (100 ml) and potassium fluoride (2.32 g, 0.04 mol) was stirred and warmed to 55° C. The two liquid phases and solid originally present became homogeneous and stayed so upon cooling. Perfluoroallyl fluorosulfate prepared as in Example 2A (10.0 g, 0.043 mol) was added rapidly at 10° C. and the mixture was allowed to warm. The slight exothermic reaction was accompanied by precipitation of solid and the appearance of a second liquid phase. The mixture was stirred for 2 hours and then poured into water (350 ml). The lower layer was washed with water (75 ml), dried over phosphorus pentoxide and distilled to give 1-{1,3-bis(2-heptafluoropropoxy)-2-pentafluoropropoxy}-pentafluoro-2-propene (16.1 g, 0.024 mol, 62%) bp 64°-67° C. (25 mm Hg) whose structure was confirmed by: $\lambda_{max}$ 5.57 (CF$_2$=CF) and 7.5–9 $\mu$m (CF, C—O); $^{19}$F NMR, −69.4 (m) 2F, OCF$_2$C=C; −80.3 (broad) 4F, CFOCF$_2$ −81.5 (s) 12F, CF$_3$, −93.7 (d J=54.0 Hz, each member d J=39.6 Hz, t J=7.8 Hz) 1F, cis-CF$_2$—CF=CF, −106.3 (d J=117.4 Hz, each member d J=54.0 Hz, t J=23.7 Hz) 1F, trans-CF$_2$CF=CF, −145.8 (m) 3F, OCF, and −190.9 ppm (d J=117.4 Hz, each member d J=39.6 Hz, t J=16.6 Hz) 1F, CF$_2$CF=C.

Anal. Calcd for $C_{12}F_{24}O_3$: C, 22.24; F, 70.35. Found: C, 22.66; F, 70.27.

EXAMPLE 5

3-(1-Pentafluoro-2-propenyloxy)tetrafluoropropionyl fluoride

A. Difluoromalonyl difluoride

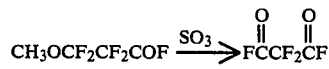

3-Methoxytetrafluoropropionyl fluoride (F. S. Fawcett, C. W. Tullock and D. D. Coffman, *J. Amer. Chem. Soc.*, 84, 4275 (1962)) (81 g, 0.45 mol) was slowly added to sulfur trioxide (80 g, 1.0 mol) at 40° C., and the product difluoromalonyl difluoride, bp −9° C., was continuously removed by distillation through a low temperature still, yield 58 g (0.40 mol, 90%). The product structure was confirmed by: $\lambda_{max}$ 1860 cm$^{-1}$ (COF), $^{19}$F NMR (no solvent), +17.1 ppm (t J=10 Hz) 2F, COF and −114.2 ppm (t J=10 Hz) 2F, CF$_2$.

B.
3-(1-Pentafluoro-2-propenyloxy)tetrafluoropropionyl fluoride

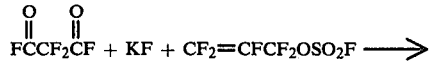

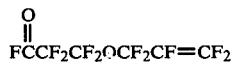

A mixture of dry potassium fluoride (7.5 g, 0.13 mol) and diglyme (100 ml) was stirred at 10° C. and difluoromalonyl difluoride from part A (18.5 g, 0.13 mol) was distilled into it. After 20 min. the potassium fluoride was nearly all dissolved, and perfluoroallyl fluorosulfate prepared as in Example 2A (29.9 g, 0.13 mol) was added dropwise at 10°-15° C. The mixture was stirred for 3 hours, then the volatile components were removed at a pot temperature of 32° C. and 4.8 mm Hg pressure. Fractionation of the distillate gave 3-(1-pentafluoro-2-propenyloxy)tetrafluoropropionyl fluoride (14.9 g, 0.051 mol, 39%) bp 70°-71° C. and a small amount of higher bp material. The product structure was confirmed by: $\lambda_{max}$ 5.33 (COF), 5.60 (CF=CF$_2$) and 7.5–10 $\mu$m (CF,C—O); $^{19}$F NMR 23.7 (apparent quintet, J~7.5 Hz) 1F, COF, −71.9 (d J=24.6 Hz, each member t J=13.9 Hz, d J=7.4 Hz) 2F, OCF$_2$C=C, −86.7 (m) 2F, CF$_2$O, −91.6 (d J=51.8 Hz, each member d J=39.4 Hz, t J=7.4 Hz) 1F, cis-CF$_2$CF=CF, −105.1 (d J=117.1 Hz, each member d J=51.8 Hz, t J=24.6 Hz) 1F, trans-CF$_2$-CF=CF, −122.0 (d J=8.2 Hz, each member t J=3.1 Hz) 2F, FCOCF$_2$, and −191.0 ppm (d, J=117.1 Hz, each member d, J=39.4 Hz, t J=13.9 Hz, t J=1.6 Hz) 1F, CF$_2$-CF=C.

Anal. Calcd for $C_6F_{10}O_2$: C, 24.51. Found: C, 24.56.

EXAMPLE 6

Perfluoro-3,6-dioxanon-8-enoyl Fluoride

A. Tetrafluorodigylcolyl Chloride

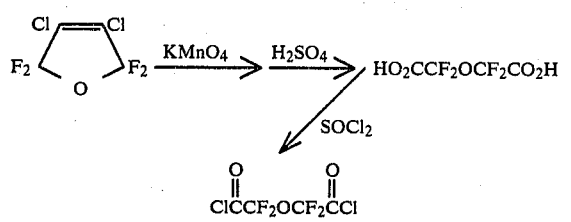

A mixture of 307.6 g (1.46 mol) of dichlorotetrafluorodihydrofuran, 157.8 g (3.9 mol) of NaOH, 312 g (1.97 mol) of potassium permanganate and 1500 ml of water was refluxed for 17 hours. A brief (steam) distillation gave 10.6 g (3%) of recovered dihydrofuran. The reaction mixture was filtered and the filter cake triturated with 2×400 ml of water. The combined aqueous solutions were evaporated to 1500 ml, treated cold with 300 ml of conc. $H_2SO_4$ and extracted continuously with ether for a day. The extracts were evaporated until ether was no longer evolved at 25° C. (0.5 mm Hg). To the crude solid diacid, 279 g (up to 93% yield), was added 5 g (0.06 mol) of pyridine and 416.5 g (3.5 mol) of thionyl chloride. Little gas evolution occurred at this stage, but considerable gas evolved as the mixture was stirred and warmed past 40° C. Evolved gases were passed through a 0° trap; after 4 hours at ca. 40° C., gassing slowed and trap contents (10 ml) were returned to the pot. The mixture was then refluxed, with occasional return of cold trap contents to the reaction, until the head temperature reached 81° C. and no gas was being evolved. Fractionation afforded 215.2 g (61% from dihydrofuran) of tetrafluorodigylcolyl chloride, bp 94°–97° C. Structure was confirmed by NMR: $^{19}F$ —77.0 ppm (s, —$CF_2O$—).

Tetrafluorodigycolyl chloride, bp 96.5° C., has previously been prepared by a different route by R. E. Banks, E. D. Burling, B. A. Dodd, and K. Mullen, J. Chem. Soc. (C), 1706 (1969).

B. Tetrafluorodigylcolyl Fluoride

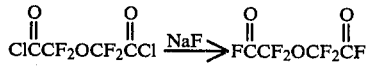

Conversion of the diacid chloride to the corresponding fluoride, bp 32°–33° C., was accomplished by a scale-up of the procedure of R. E. Banks, E. D. Burling, B. A. Dodd, and K. Mullen, J. Chem. Soc. (c), 1706 (1969). A mixture of 215 g (0.885 mol) of tetrafluorodiglycolyl dichloride, 140.5 g (3.35 mol) of NaF, and 1200 ml of anhydrous acetonitrile was stirred overnight, then distilled to give a fraction collected at 35°–79° C. The distillate was treated with 20 g of NaF and distilled to give 105 g of tetrafluorodiglycolyl difluoride, bp 32°–33° C. Addition of another 100 g (2.38 mol) of NaF to the reaction mixture and slow distillation afforded another fraction, bp 35°–81° C. Treatment with 10 g of NaF and fractionation gave another 37.0 g of difluoride product, bp 32°–33° C., for a total of 142 g (76%).

C. Perfluoro-3,6-dioxanon-8-enoyl Fluoride

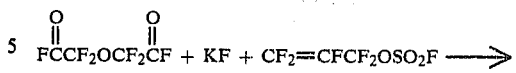

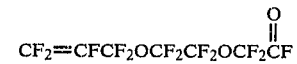

A mixture of 38.9 g (0.67 mol) of KF, 141.5 g (0.67 mol) of tetrafluorodiglycolyl difluoride, and 500 ml of dry diglyme was stirred for 30 minutes at 5° C., during which time nearly all of the KF dissolved. Then 154.1 g (0.67 mole) of perfluoroallyl fluorosulfate was added rapidly at 5° C. and the mixture was stirred at 0°–5° C. for 3 hours, at 25° C. for 2 hours, and allowed to stand overnight. Volatiles were evaporated to diglyme reflux at 38° C. (3 mm Hg). Distillation of volatiles from 20 g of NaF gave 28.2 g (20%) of recovered diacid fluoride, bp 32°–33° C., and 125.0 g (52%) of monoacid fluoride, almost all of it bp 93°–94° C. Structure was confirmed by:

ir ($CCl_4$): 5.30 (COF), 5.59 (C=C), 8–9μ (CF, C—O). NMR: F 13.3 (m, 1 F, COF), −72.0 (d of d of t of d, $J_{FF}$ 25, 13, 13, 7.7 Hz, 2F, =$CFCF_2$), −77.5 (t of d, $J_{FF}$ 11.5, 2.7 Hz, 2 F, $CF_2CO_2F$), −88.8 (t, $J_{FF}$ 11.5 Hz, 2 F, $CF_2OCF_2COF$), −89.4 (t, $J_{FF}$ 12.7 Hz, 2 F, =$CFCF_2OCF_2$), −91.9 (d of d of t, $J_{FF}$ 52.7, 39.3, 7.7 Hz, 1F, cis-$CF_2CF$=$CF$), −105.3 (d of d of t, $J_{FF}$ 117.6, 52.7, 24.6 Hz, 1 F, trans-$CF_2CF$=$CF$), and −190.8 ppm (d of d of t of t, $J_{FF}$ 117.6, 39.3, 13.7, 1.6 Hz, 1 F, $CF_2CF$=).

EXAMPLE 7

2-(1-Pentafluoro-2-propenyloxy)tetrafluoroethanesulfonyl fluoride

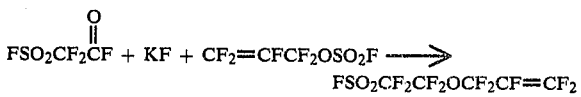

A suspension of potassium fluoride (5.8 g, 0.10 mol) in diglyme (100 ml) was stirred and cooled while fluorosulfonyldifluoroacetyl fluoride (18.0 g, 0.10 mol) (D. C. England, M. A. Dietrich and R. V. Lindsey, Jr., J. Amer. Chem. Soc., 82 6181 (1960)) was added rapidly. The mixture was stirred for 15 min at 20°–30° C. during which time the potassium fluoride dissolved, and then it was treated with perfluoroallyl fluorosulfate prepared as in Example 2A (25.0 g, 0.11 mol) at 20°–25° C. over 5 min. The mixture was stirred for 2 hours, during which time solid precipitated, and the temperature rose to 28° C. and fell again. The volatile components were transferred to a trap cooled to −80° C. by warming the solution to reflux at 38° C. (5 mm Hg). The distillate was treated with concentrated sulfuric acid (10 ml) to remove diglyme, then distilled to give 2-(1-pentafluoro-2-propenyloxy)tetrafluoroethanesulfonyl fluoride (19.9 g, 0.06 mol, 60%) bp 55°–56° C. (150 mm Hg). The product structure was confirmed by: $\lambda_{max}$ 5.53 ($CF_2$=CF), 6.79 ($SO_2F$) and 7-10 μm (CF,C—O,$SO_2$); $^{19}F$ NMR, +44.9 (t J=6 Hz, each member t J=6 Hz) 1F, $FSO_2$, −71.8 (d J=25.3 Hz, each member t J=13.8 Hz, d J=13.8 Hz, d J=7.3 Hz) 2F, $OCF_2C$=C, −83.0 (m) 2F, $CF_2CF_2O$, −90.9 (d J=50.6 Hz, each member d J=39.5 Hz, t J=7.3 Hz) 1F, cis-$CF_2CF$=$CF$, −104.5

(d J=117.6 Hz, each member d J=50.6 Hz, t J=25.3 Hz) 1F, trans-CF$_2$CF=C$\underline{F}$, −113.0 (d J=5.6 Hz, each member t J=2.9 Hz) 2F, FSO$_2$C$\underline{F}_2$, and −190.9 ppm (d J=117.6 Hz, each member d J=39.5 Hz, t J=13.8 Hz, t J=3.2 Hz) 1F, CF$_2$C$\underline{F}$=C.

Anal. Calcd for C$_5$F$_{10}$O$_3$S: C, 18.19; F, 57.55; S, 9.71. Found: C, 18.35; F, 57.40; S, 9.69.

EXAMPLE 8

2-(1-Pentafluoro-2-propenyloxy)tetrafluoroethanesulfonyl fluoride

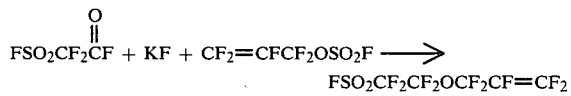

The procedure of Example 7 was followed, substituting acetonitrile for diglyme as the solvent. The acetonitrile was not rigorously purified, and the yields of 2-(1-pentafluoro-2-propenyloxy)tetrafluoroethanesulfonyl fluoride, pb 54°–55° C. (150 mm Hg) ranged from 40–50%.

EXAMPLE 9

1-[1-(Pentafluoro-2-propenyloxy)]hexafluoropropane-2-sulfonyl fluoride

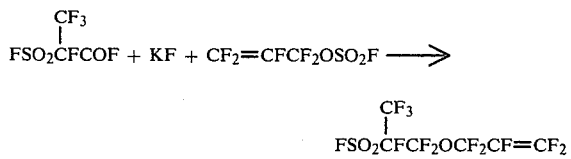

A mixture of potassium fluoride (5.80 g, 0.10 mol) and diglyme (100 ml) was stirred at 10° C. while 2-fluorosulfonyltetrafluoropropionyl fluoride (23.0 g, 0.10 mol) (D. C. England, M. A. Dietrich and R. V. Lindsey, Jr., J. Amer. Chem. Soc., 82 6181 (1960)) was added. The resulting solution was treated at 10° C. with perfluoroallyl fluorosulfate prepared as in Example 2A, and after the addition was complete, the mixture was stirred at 25° C. for 3 hours, then it was poured into water (500 ml). The lower layer was washed with water (100 ml), dried and distilled to give 1-[1-(pentafluoro-2-propenyloxy)]hexafluoropropane-2-sulfonyl fluoride (25.7 g, 0.068 mol, 68%) bp 50° C. (60 mm Hg), pure by gas liquid partition chromatography (glpc). The product structure was confirmed by: $\lambda_{max}$ 5.55 (CF=CF$_2$), 6.78 (SO$_2$F) and 7.5–10 μm (CF,C—O,SO$_2$); $^{19}$F NMR, 54.9 (d J=20.7 Hz, each member q of J=10.4 Hz, d J=3.6 Hz) 1F, SO$_2$F, −71.8 (d J=25.0 Hz, each member t J=13.8 Hz, d J=13.8 Hz, d J=7.4 Hz) 2F, OCF$_2$C=C, −72.1 (m) 3F, CF$_3$, −75.5 (m) 2F, CFC$\underline{F}_2$O, −91.0 (d J=50.7 Hz, each member d J=39.4 Hz, t J=7.4 Hz) 1F, cis-CF$_2$CF=C$\underline{F}$, −104.6 (d J=117.6 Hz, each member d J=50.7 Hz, t J=25.0 Hz) 1F, trans-CF$_2$CF=C$\underline{F}$, −166.4 (d J=14.6 Hz, each member q J=7.2 Hz, d J=3.6 Hz) 1F, CF, and −191.1 ppm (d J=117.6 Hz, each member d J=39.4 Hz, t J=13.8 Hz, t J=1.7 Hz) 1F CF$_2$C$\underline{F}$=C.

Anal. Calcd for C$_6$F$_{12}$O$_3$S: C, 18.96; F, 59.98; S, 8.44. Found: C, 18.70; F, 60.09; S, 8.08.

EXAMPLE 10

Perfluoro(4-oxa-6-heptenenitrile)

A. 3-Methoxytetrafluoro-propionamide

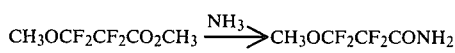

A solution of 140 g (0.74 mol) of methyl 3-methoxytetrafluoropropionate in 100 ml of ether was treated at 0° with 15.3 g (0.90 mol) of NH$_3$. The resulting viscous mixture was stirred at 25° overnight and evaporated to dryness at 25° (10 mm). The crude residue was then recrystallized from ether/hexane to give 123.6 g (95%) of 3-methoxytetrafluoropropionamide, mp 78°–80°. An analytical sample was recrystallized from ether/hexane, mp 83°–85°. IR (KBr): 2.95, 3.02 and 3.10 (NH$_2$), 3.37 and 3.49 (sat'd CH), 5.92 (C=O), 6.19 (NH$_2$), 7.5–10μ (CF, C—O). NMR ((CD$_3$)$_2$CO): $^1$H 6.67 (broad, 2H, NH$_2$) and 3.66 ppm (s, 3H, OCH$_3$); $^{19}$F −120.6 (t, J$_{FF}$ 4.7 Hz, 2F, CF$_2$) and −121.8 ppm (t, J$_{FF}$ 4.7 Hz, of d, J$_{HF}$ 2.1 Hz, 2F, CF$_2$).

Anal. Calcd. for C$_4$H$_5$F$_4$NO$_2$: C, 27.44; H, 2.88; N, 8.00. Found: C, 27.74; H, 2.93; N, 7.99.

B. 3-methoxytetrafluoropropionitrile

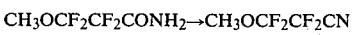

A solution of 52.5 g (0.30 mol) of the amide from Part A in 200 ml of diglyme was stirred at −10° while 47.5 g (0.60 mol) of pyridine and 63.0 g (0.30 mol) of trifluoroacetic anhydride were added. The cooling bath was removed, and the mixture was stirred at ca 25° for 2 hr. Evaporation of volatiles to 40° (4.5 mm) gave 42.7 g of crude product, which was distilled to afford 36.5 g (77%) of 3-methoxytetrafluoropropionitrile, bp 53°. IR (neat): 3.36 and 3.48 (sat'd CH), 4.42 (CN), 8–10μ (CF, C—O). NMR: $^1$H 3.78 ppm (s, OCH$_3$); $^{19}$F −93.2 (t, J$_{FF}$ 6.3 Hz, 2F, CF$_2$) and −108.8 ppm (t, J$_{FF}$ 6.3 Hz, 2F, CF$_2$).

Anal. Calcd. for C$_4$H$_3$F$_4$NO: C, 30.59; H, 1.92; N, 8.92. Found: C, 30.83; H, 1.94; N, 8.77.

C. Cyanodifluoroacetyl fluoride

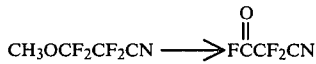

When 55.5 g (0.69 mol) of SO$_3$ was added to 109 g (0.69 mol) of nitrile prepared as in Part B, a mild exothermic reaction ensued. The mixture was stirred 2 hr, then heated at reflux (50°) for 4 hr, during which time the pot temperature rose from 73° to 91° and some volatiles were collected in the −80° trap. Distillation gave 19.1 g (18% assuming pure) of recovered nitrile and 67.3 g (86%) of methyl fluorosulfate. The bath temperature was taken ultimately to 170°. Considerable tarry residue and 22 ml at −80° of volatile products were also formed. Distillation of the volatiles gave 17 g (20% conversion) of cyanodifluoroacetyl fluoride, bp 8°. IR (gas phase): 4.42 (CN), 5.27 (COF), 8–10μ (CF) with small amounts of SO$_2$ and an unknown impurity present. NMR: $^{19}$F +16.7 (t, J$_{FF}$ 11.0 Hz, 1F, COF) and −98.0 ppm (d, J$_{FF}$ 11.0 Hz, 2F, CF$_2$). Mass spec: m/c 122.9926 (M+; calcd. for C F NO, 122.9932), 103.9939

($M^+$-F; calcd. for C F NO, 103.9949), 75.9961 (CF CN$^+$; calcd. for C F N, 75.9999).

D. Perfluoro(4-Oxa-6-heptenenitrile)

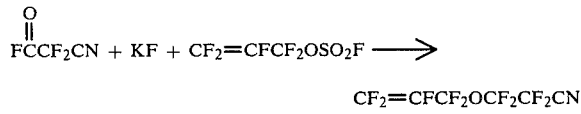

To a suspension of 9.0 g (0.156 mol) of flamedried KF in 200 ml of dry diglyme at −10° was added 16 g (0.13 mol) of cyanodifluoroacetyl fluoride from part C. The mixture was stirred at 0° for 30 min, after which it was homogeneous. Then 33.9 g (0.15 mol) of $CF_2$=$CFCF_2OSO_2F$ was added at 0°, and the mixture was stirred at 0°-5° for 4 hr, then at 25° for 1 hr. Volatiles were removed at 40° (5 mm) and fractionated to give 22.4 g (63%) of perfluoro(4-oxa-6-heptenenitrile), bp 66°-67°. IR (CCl$_4$): 4.31 (CN), 5.61 (CF=CF$_2$), 8-10μ (CF, C—O). NMR: $^{19}$F −71.9 (d of d of t of d, $J_{FF}$ 25.0, 13.6, 12.7, 7.3 Hz, 2F, OCF$_2$C=), −88.1 (t of t of m, $J_{FF}$ 12.7, 5.0 Hz, 2F, OCF$_2$CF$_2$), −90.9 (d of d of t, $J_{FF}$ 50.3, 39.1, 7.3 Hz, 1F, cis-CF$_2$CF=CFF), −104.5 (d of d of t, $J_{FF}$ 116.6, 50.3, 25.0, 1F, trans-CF$_2$CF=CFF), −109.3 (t, $J_{FF}$ 5.0 Hz, 2F, CF$_2$CN), and −190.9 ppm (d of d of t of m, $J_{FF}$ 116.6, 39.1, 13.6 Hz, 1F, CF$_2$CF=).

Anal. Calcd. for $C_6F_9NO$: C, 26.39; N, 5.13. Found: C, 26.37; N, 5.31.

EXAMPLE 11

Methyl Perfluoro(5-methyl-4,7-dioxa-9-decenoate)

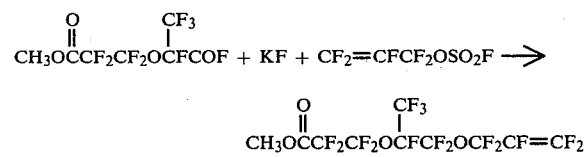

Condensation of 5-carbomethoxyperfluoro(2-methyl-3-oxavaleroyl) fluoride with KF/CF$_2$=CFCF$_2$OSO$_2$F was demonstrated by adding 16.1 g (0.50 mol) of it to a suspension of 32.0 g (0.55 mol) of flame dried KF in 500 ml of dry diglyme stirred at 0°. The mixture was stirred at 0°-10° for 10 min, after which most of the KF had dissolved. Then 126.5 g (0.55 mol) of CF$_2$=CFCF$_2$OSO$_2$F was added rapidly, and the mixture was stirred at 5°-10° for 3 hour, then 1 hr at 25°. The reaction mixture was poured into 2 l. of water, and the lower layer was washed with water, extracted with 25 ml of conc. H$_2$SO$_4$, clarified with CaSO$_4$, filtered and distilled to give 63.7 g (27%) of methyl perfluoro(5-methyl-4,7-dioxa-9-decenoate), bp 61°-62° (10 mm). IR (neat): 3.31, 3.37, and 3.48 (sat'd CH), 5.58 (broad; C=O, CF=CF$_2$), 7-10μ (CF, C—O). NMR: $^1$H 3.93 ppm (s, OCH$_3$); $^{19}$F −72.0 (m, 2F, CF$_2$C=), −80.6 (m, 3F, CF$_3$), −83.4 (m, 2F, CF$_2$O), −83.9 (m, 2F, CF$_2$O), −91.9 (d of d of t, $J_{FF}$ 52.7, 39.5, 7.4 Hz, 1F, cis-CF$_2$CF=CFF), −105.2 (d of d of t, $J_{FF}$ 117.3, 52.7, 25.0 Hz, 1F, trans-CF$_2$CF=CFF), −122.0 (t, $J_{FF}$ 3.1 Hz, 2F, CF$_2$C=O), −145.9 (t, $J_{FF}$ 20.5 Hz, of m, 1F, CF) and −191.1 ppm (d of d of t, $J_{FF}$ 117.3, 39.5, 13.9 Hz, 1F, CF$_2$CF=CF$_2$).

Anal. Calcd. for $C_{10}H_3F_{15}O_4$: C, 25.44; H, 0.64. Found: C, 25.57; H, 0.66.

EXAMPLE 12

A. Perfluoro(3-allyloxyglutaroyl)Fluoride and Perfluoro(3-keto-6-oxa-8-nonenoyl)fluoride

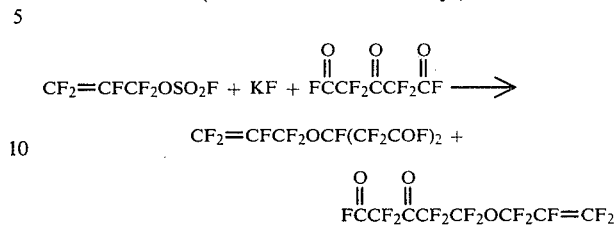

To a suspension of 29.0 g (0.50 mol) of flamedried KF in 600 ml of diglyme stirred at 0° was added 111.0 g (0.50 mol) of 3-ketotetrafluoroglutaroylfluoride prepared by the action of SO$_3$ on bis(2-methoxytetrafluoroethyl)ketone. The mixture was stirred for 30 min at 0°-5°, when nearly all of the KF had dissolved. Then 115 g (0.50 mol) of perfluoroallyl fluorosulfate was added dropwise, and the mixture was stirred at 0°-5° for 4 hr, warmed slowly to 25°, and volatiles removed to 40° (5 mm) in the pot. The volatiles, 135.2 g, were distilled to give fractions, bp 45°-61° (100 mm), 105.2 g (57% crude), of which 100 g had bp 59°-61° (100 mm) and was indicated by gc to contain one major component and minor (0-15%) amounts of a second product. IR (CCl$_4$): 5.31 (COF), 5.57 (CF=CF$_2$, C=O), 7.2-10μ (CF, C—O). For a late fraction, bp 61° (100 mm), of nearly pure perfluoro(3-allyloxyglutaroyl)fluoride, NMR (CCl$_4$): $^1$H v. small amount diglyme impurity; $^{19}$F 24.6 (m, 2F, COF), −68.5 (m, 2F, OCT$_2$C=), −91.2 (d of d of t, $J_{FF}$ 51.4, 39.5, 7.3 Hz 1F, cis-CF$_2$CF=CFF), −104.8 (d of d of t, $J_{FF}$ 117.6, 51.4, 25.2 Hz, 1F, trans-CF$_2$CF=CFF), −116.1 (m, 4F, CF$_2$C=O), −141.2 (m, 1F, CF), and −190.8 ppm (d of d of d of t, $J_{FF}$ 117.6, 39.5, 13.5 Hz, 1F, CF$_2$CF=). An earlier fraction contained 2% of a second fluorinated component identified as perfluoro(3-keto-6-oxa-8-nonenonyl)fluoride by $^{19}$F NMR.

B. Dimethyl Perfluoro-3-allyloxyglutarate and Methyl Perfluoro(3-keto-6-oxa-8-nonanoate)

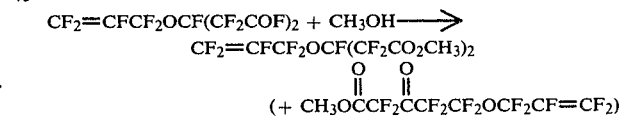

Perfluoro(3-allyloxyglutaroyl)fluoride from Part A was easily converted to its dimethyl ester by treatement at 25°-40° with a mixture of methanol and NaF. Filtration and distillation gave pure dimethyl perfluoro(3-allyloxyglutarate), bp 77° (0.70 mm), identified by comparison of its IR spectrum with that of an authentic sample, in 42% overall yield from 3-ketotetrafluoroglutaroyl fluoride. Since the coproduct, methyl perfluoro-(3-keto-6-oxa-8-nonanoate), is considerably lower boiling, it was easily separated during the fractionation.

EXAMPLE 13

Perfluoro-1,6-bis(2-propenyloxy)hexane

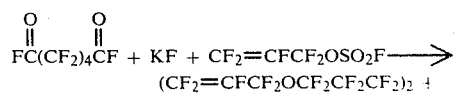

-continued

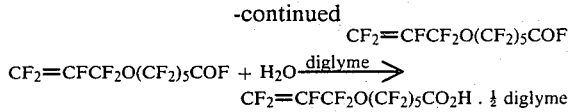

A mixture of potassium fluoride (11.62 g, 0.20 mol), diglyme (200 ml) and octafluoroadipoyl difluoride (PCR 28.2 g, 0.096 mol) was stirred at 5° C. for 1.5 hours. The mixture was kept at 5°-10° C. while perfluoroallyl fluorosulfate prepared as in Example 2A (46.0 g, 0.20 mol) was added dropwise. When the addition was complete, the mixture was stirred at 5° C. for 30 min, then it was allowed to warm to 25° C. and the stirring was continued for a further 3 hours. After having stood overnight, the mixture was poured into water (1 l.); the lower layer was washed with water (150 ml), dried and distilled to give two products.

The lower-boiling fraction was perfluoro-1,6-bis(2-propenyloxy)hexane (21.1 g, 0.0355 mole, 37%), bp 84°-86° C. (20 mm Hg) whose structure was confirmed by: $\lambda_{max}$ 5.59 ($CF=CF_2$) and 7.2-9.5 µm (C—F, C—O): $^{19}F$ NMR, −72.1 (d J=25.7 Hz, each member t J=13.3 Hz, d J=13.3 Hz, t J=7.6 Hz) 2F, $OCF_2C=C$, −84.2 (m) 2F, $CF_2O$, −92.3 (d J=52.7 Hz, each member d J=39.5 Hz, t J=7.6 Hz) 1F, cis-$CF_2CF=CF$, −105.5 (d J=117.8 Hz, each member d J=52.7 Hz, t J=−25.7 Hz) 1F, trans-$CF_2CF=CF$, −122.9 (m), $CF_2$, −126.2 (m) 2F, $CF_2$, and −191.0 ppm (d J=117.8 Hz, each member d J=39.5 Hz, t J=13.8 Hz) 1F, $CF_2-CF=C$.

Anal. Calcd for $C_{12}F_{22}O_2$: C, 24.26; F, 70.35. Found: C, 24.43; F, 70.38.

The higher boiling fraction was the 2:1 complex of perfluoro-6-(2-propenyloxy)hexanoic acid with diglyme (7.9 g, 0.0155 mol, 16%), bp 109°-110° C. (5 mm Hg), formed by hydrolysis of perfluoro-6-(2-propenyloxy)hexanoyl fluoride in the aqueous diglyme wash solutions. This complex had $\lambda_{max}$ 3-4 (OH, C—H), 5.59 (with shoulder, $CF_2=CF$, $CO_2H$), and 7.2-9 µm (CF, C—O, CH); $^1H$ NMR, δ 11.93 (s) 1H, $CO_2H$, 3.75 (s) 4H, $OCH_2$, and 3.52 (s) 3H, $OCH_3$; $^{19}F$ NMR, −71.9 (d J=25.1 Hz, each member t J=13.4 Hz, d J=13.4 Hz, d J=7.5 Hz) 2F, $OCF_2C=C$, −84.1 (m) 2F, $CF_2CF_2O$, −92.0 (d J=52.3 Hz, each member d J=39.3 Hz, t J=7.4 Hz) 1F, cis-$CF_2CF=CF$, −105.2 (d J=117.7 Hz, each member d J=52.3 Hz, t J=25.1 Hz), 1F, trans-$CF_2CF=CF$, −119.6 (t J=12.6 Hz, each member t J=3.2 Hz) 2F, $CF_2$, −122.6 (m) 2F, $CF_2$, −123.5 (m) 2F, $CF_2$, −126.1 (m) 2F, $CF_2$, and −190.9 ppm (d J=117.7 Hz, each member d J=39.3 Hz, t, J=13.8 Hz, t J=1.8 Hz 1F, $CF_2CF=C$.

EXAMPLE 14

Methyl Perfluoro-3,6-dioxanon-8-enoate

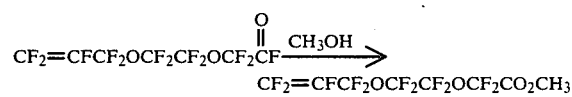

A suspension of 42 g (1.0 mol) of NaF in 100 ml of methanol was stirred at 5° C. while 114 g (0.317 mol) of acid fluoride was added rapidly. After addition had been completed, the mixture was stirred overnight at 25° C., filtered and the solid rinsed with ether. Distillation afforded 102.0 g (86%) of methyl perfluoro-3,6-dioxanon-8-enoate, bp 60°-61° C. (20 mm Hg), containing small amounts of impurities. Redistillation gave somewhat more pure ester (1-2% impurities by gc), bp 61°-62° C. (20 mm Hg). Structure was confirmed by Ir (neat): 3.32, 3.37, 3.49 ($CH_3$), 5.57 (C=O), 8-9.5µ (CF, C—O). NMR: H 3.95 ppm (s) with small impurites at 3.53 and 3.33 ppm; $^{19}F$ −72.0 (d of d of t of d, $J_{FF}$ 24, 13, 13, 7.5 Hz, 2 F, =$CFCF_2$), −78.0 (t, $J_{FF}$ 11.6 Hz, 2 F, $CF_2CO_2CH_3$), −89.0 (t, $J_{FF}$ 11.6 Hz, 2 F, $CF_2OCF_2CO_2CH_3$), −89.5 (t, $J_{FF}$ 12.6 Hz, 2 F, =$CFCF_2OCF_2$), −92.3 (d of d of t, $J_{FF}$ 53.2, 39.2, 7.5 Hz, 1 F, cis-$CF_2CF=CF$), −105.2 (d of d of t, $J_{FF}$ 117.3, 53.2, 24.3 Hz, 1F, trans-$CF_2CF-CF$), and −190.8 ppm (d of d of t of t, $J_{FF}$ 117.3, 39.2, 14.0, 1.6 Hz, 1 F, $CF_2CF=$).

Anal. Calcd. for $C_8H_3F_{11}O_4$: C, 25.82; H, 0.81; F, 56.17. Found: C, 26.17; H, 0.66; F, 56.24.

EXAMPLE 15

Dimethyl Perfluoro-3-alloxyglutarate

A. 1,3,3,5-Tetramethoxyoctafluoropentane

The synthesis of bis(2-methoxytetrafluoroethyl)ketone from dimethyl carbonate tetrafluoroethylene, and sodium methoxide has been described by D. W. Wiley (U.S. Pat. No. 2,988,537 (1961)). An extension of this synthesis has given 1,3,3,5-tetramethoxyoctafluoropentane in a one-pot reaction.

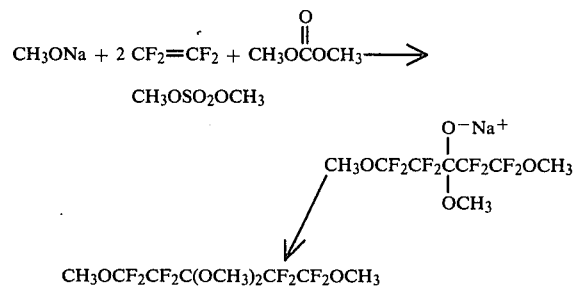

A mixture of 27.0 g (0.50 mol) of sodium methoxide, 56.0 g (0.62 mol) of dimethyl carbonate, and 100 ml of dry tetrahydrofuran was agitated in a 350 ml tube under 1-3 atm of tetrafluoroethylene. Tetrafluoroethylene was pressured in as consumed until 110 g (1.1 mol) had been added. The mildly exothermic reaction kept the temperature near 35° C.; after the addition, the reaction mixture was heated at 40° C. for 1 hour. The viscous solution from this reaction was treated directly with 75.6 g (0.60 mol) of dimethyl sulfate at 40° C. for 15 hours. Filtration and distillation afforded 87.6 g (52%) of 1,3,3,5-tetramethoxyoctafluoropentane, bp 54° C. (0.3 mm Hg), $n_D^{24}$ 1.3605, whose structure was confirmed by IR 3.29, 3.33, and 3.42 (satd CH) 8−9µ (CF, COC). Nmr ($CCl_4$) $^1H$ δ 3.68 (s, 1, $CF_2OCH_3$) and 3.57 (p, $J_{HF}$ 1.3 Hz, 1, C $(OCH_3)_2$); $^{19}F$ −88.2 (m, l, $CF_2O$) and −116.5 ppm (m, l, $CF_2$).

Anal. Calcd. for $C_9H_{12}F_8O_4$: C, 32.16; H, 3.60; F, 45.21. Found: C, 32.57; H, 3.72; F, 44.61.

B. Dimethyl Tetrafluoroacetone-1,3-dicarboxylate

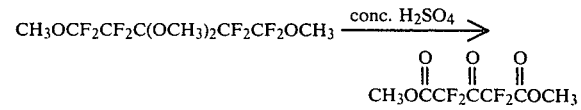

To 50 ml of conc. $H_2SO_4$ was added dropwise 33.6 g (0.10 mol) of the tetraether. After the mildly exothermic reaction had subsided, the mixture was heated at 70° C.

(50 mm Hg) to remove volatiles and then distilled at ca. 50° C. (1 mm Hg). The crude distillate was then fractionated to afford 16.9 g (69%) of dimethyl tetrafluoroacetone-1,3-dicarboxylate, bp 58° C. (2 mm), $n_D^{22}$ 1.3713. Structure was confirmed by Ir 3.28, 3.34 and 3.48 (satd CH), 5.57 (C=O) 5.64 (sh-C=O), 8-9μ (CF, COC) Nmr (CCl$_4$) 'H δ 4.00 (s, OCH$_3$); $^{19}$F −113 ppm (s, CF$_2$).

Anal. Calcd. for C$_7$H$_6$F$_4$O$_5$: C, 34.16; H, 2.46; F, 30.88 mol wt, 246. Found: C, 34.18; H, 2.66; F, 30.95; mol wt, 246 (mass spec).

The same reaction on a 0.56 mole scale gave the diester in 82% yield.

C. Dimethyl Perfluoro-3-alloxyglutarate

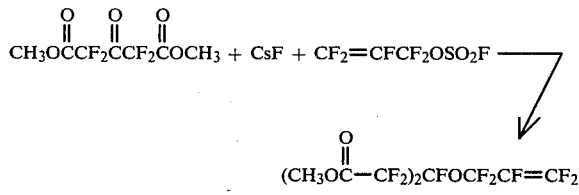

To 27.3 g (0.18 mol) dry CsF in 100 ml diglyme was added 43.5 g (0.18 mol) O=C(CF$_2$COOCH$_3$)$_2$ at 5°-10° C. and stirred for 1 hour; 41.4 g (0.18 mol) CF$_2$=CFCF$_2$OSO$_2$F was added at 5°-10° C. and the mixture was stirred further for 3 hours. The reaction mixture was thrown into 1 liter of H$_2$O and the lower layer separated. This was washed twice with H$_2$O. After treatment with 20 ml H$_2$SO$_4$ at 0° C. and extraction with Freon® 113, the extract was distilled in a molecular still to give 4.54 g (7.2% yield) of product, bp=51°-53° C. (0.1 mm). Structure was confirmed by $^{19}$F nmr (F11): −68.48 ppm (OCF$_2$CF=); −93.45 ppm cis-(CF=CFF); −105.91 ppm trans-(CF=CF); −117.10 ppm (CF$_2$COOCH$_3$); −142.78 ppm (CF$_2$CF$_2$OCF=); −190.35 ppm (CF=CF$_2$). 'H nmr (F11/TMS): 3.96 (singlet, CH$_3$). Ir (neat): 3.37μ, 3.49μ (sat CH); 5.60 2 (>C=O, CF$_2$=CF); 8-10μ (CF, CO).

Anal. Calcd for C$_{10}$F$_{10}$H$_6$O$_5$: C, 30.32; F, 47.96; H, 1.33. Found: C, 30.45; F, 48.10; H, 1.48.

EXAMPLE 16

Perfluoro-3-(2-propoxy-2-methylethoxy)propene

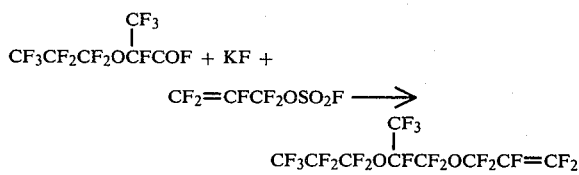

A mixture of potassium fluoride (6.96 g, 0.12 mol), diglyme (150 ml) and 2-(1-heptafluoropropoxy)tetrafluoropropionyl fluoride (dimer of hexafluoropropene oxide obtained by treatment with fluoride ion) (29.4 g, 0.089 mol) was stirred at 5° C. for 1 hour. Perfluoroallyl fluorosulfate prepared as in Example 2A (27.6 g, 0.12 mol) was added dropwise at 5° C., then the mixture was stirred at 5° C. for 3 hours, and at 25° C. overnight. The reaction mixture was poured into water (1 l.), the lower layer was separated and the volatile components were removed at 25° C. (0.5 mm Hg). Distillation of the volatile components from concentrated sulfuric acid gave perfluoro-3-(2-propoxy-2-methylethoxy)propene (25.2 g, 0.052 mol, 59%), bp 62°-63° C. (100 mm Hg) whose structure was confirmed by: λ$_{max}$ 5.57 (CF=CF$_2$) and 7.5-9 μm (C—F, C—O); $^{19}$F NMR, −72.2 (d J=25.5 Hz, each member t J=13.3 Hz, d J=13.3 Hz, d J=7.4 Hz) 2F, OCF$_2$ C=C, −81.0 (m) 3F, CF$_3$, −82.3 (m) 5F, CF$_3$+OCF$_2$, −84.1 (m) 2F, CF$_2$O, −92.1 (d J=52.7 Hz, each member d J=39.7 Hz, t J=7.4 Hz) 1F, cis-CF$_2$CF=CF, −105.5 (d J=117.8 Hz, each member d J=52.7 Hz, t J=25.5 Hz), 1F, trans-CF$_2$CF=CF, −130.4 (s) 2F, CF$_2$, −145.9 (m) 1F, CF, and −191.0 ppm (d J=117.8 Hz, each member d J=39.7 Hz, t J=13.6 Hz) 1F, CF$_2$CF=C.

Anal. Calcd for C$_9$H$_{18}$O$_2$: C, 22.42; F, 70.94. Found: C, 22.18; F, 70.96.

EXAMPLE 17

Perfluoro-1,3-bis(2-propenyloxy)propane

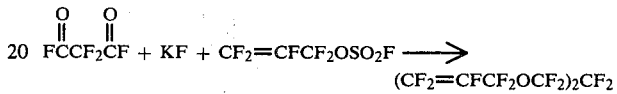

A mixture of potassium fluoride (15.3 g, 0.26 mol), diglyme (200 ml) and difluoromalonyl difluoride prepared as in Example 5A (17.3 g, 0.12 mol) was stirred at 5° C. for 15 min. Perfluoroallyl fluorosulfate (57.5 g, 0.25 mol) was added at 5°-10° C. over a 45 min period, and the mixture was stirred at 5° C. for an additional hour, then at 25° C. for 2 hours. The reaction mixture was poured into water (1 l.), the lower layer was washed with water (100 ml), dried and distilled to give perfluoro-1,3-bis (2-propenyloxy)propane (12.0 g, 0.027 mol, 23%) bp 88°-90° C. (200 mm Hg) whose structure was confirmed by: λ$_{max}$ 5.59 (CF=CF$_2$) and 7.2-9.5 μm (C—F, C—O); $^{19}$F NMR, −72.2 (m) 2F, OCF$_2$C=C, −84.6 (m) 2F, CF$_2$CF$_2$O, −92.3 (d J=53.0 Hz, each member d J=39.5 Hz, t J=7.2 Hz) 1F, cis-CF$_2$CF=CF, −105.6 (d J=117.8 Hz, each member d J=53.0 Hz, t J=25.2 Hz) 1F, trans-CF$_2$CF=CF, −130.0 (s) 1F, CF$_2$ and −191.0 ppm (d J=117.8 Hz, each member d J=39.5 Hz, t J=13.5 Hz) 1F, CF$_2$CF=C.

Anal. Calcd for C$_9$F$_{16}$O$_2$: C, 24.34; F, 68.45. Found: C, 24.67; F, 68.36.

EXAMPLE 18

Perfluoro-3-(butoxy)propene

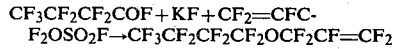

A mixture of dry potassium fluoride (7.50 g, 0.13 mol), diglyme (100 ml) and heptafluorobutyroyl fluoride (prepared from the acid by treatment with sulfur tetrafluoride) (28.1 g, 0.13 mol) was stirred at 5° C. for 30 min. Perfluoroallyl fluorosulfate was added dropwise at 5° C., the mixture was stirred at this temperature for 1 hour, then at 25° C. for 3 hours. The volatile components were transferred by distillation at 40° C. (8 mm Hg), washed with water (100 ml), and distilled from a small amount of concentrated sulfuric acid to give perfluoro-3-(butoxy)propene (30.3 g, 0.083 mol, 64%) bp 80°-84° C. whose structure was confirmed by: λ$_{max}$ 5.57 (CF=CF$_2$) and 7.2-9.5 μm (C—F, C—0); $^{19}$F NMR −72.1 (d J=25.2 Hz, each member t J=13.5 Hz, d J=13.5 Hz, d J=7.4 Hz) 2F, OCF$_2$C=C, −82.1 (t J=8.1 Hz, each member m), 3F, CF$_3$, −84.5 (m) 2F, CF$_2$O, −92.1 (d J=52.3 Hz, each member d J=39.4

Hz, t J=7.4 Hz) 1F, cis-CF$_2$CF=C$\underline{F}$, −105.5 (d J=117.5 Hz, each member d J=52.3 Hz, t J=25.2 Hz) 1F, trans-CF$_2$CF=C$\underline{F}$, −127.3 (m) 4F, CF$_2$, and −191.0 ppm (d J=117.5 Hz, each member d J=39.4 Hz, t J=13.7 Hz, m) 1F, CF$_2$C$\underline{F}$=C.

Anal. Calcd for C$_7$F$_{14}$O: C, 22.97; F, 72.66. Found: C, 23.20; F, 72.80.

EXAMPLE 19

Perfluoro-3-(octyloxy)propene

F(CF$_2$)$_7$COF+KF+CF$_2$=CFC-F$_2$OSO$_2$F→F(CF$_2$)$_8$OCF$_2$CF=CF$_2$

A mixture of potassium fluoride (5.80 g, 0.10 mol), diglyme (150 ml) and pentadecafluorooctanoyl fluoride (prepared by treating commercial perfluorooctanoic acid with sulfur tetrafluoride) (25.0 g, 0.06 mol) was stirred at 5° C. for 1 hour. Perfluoroallyl fluorosulfate (23.0 g, 0.10 mol) was added dropwise and the mixture was stirred at 5° C. for 4 hours, then at 25° C. for an additional 3 hours. The mixture was poured into water (1 l.), separated, and the lower layer was distilled from concentrated sulfuric acid to give perfluoro-3-(octyloxy)propene (27.1 g, 0.048 mol, 80%) bp 69°–70° C. (20 mm Hg) whose structure was confirmed by: λ$_{max}$ 5.59 (CF=CF$_2$) and 8–9 μm (CF C—O); $^{19}$F NMR −71.8 (d J=25.1 Hz, each member d J=13.4 Hz, t J=13.4 Hz, d J=7.7 Hz) 2F, OCF$_2$C=C, −81.6 (t J=10.0 Hz) 3F, CF$_3$, −83.8 (m) 2F, CF$_2$C$\underline{F}_2$O, −92.3 (d J=53.6 Hz, each member d J=39.9 Hz, t J=7.7 Hz) 1F, cis-CF$_2$CF=C$\underline{F}$, −105.5 (d J=117.8 Hz, each member d J=53.5 Hz, t J=25.1 Hz) 1F, trans-CF$_2$CF=C$\underline{F}$, −122.2 (m) 6F, CF$_2$, −122.9 (m) 2F, CF$_2$, −125.7 (m) 2F, CF$_2$, −126.5 (m) 2F, CF$_2$, and −190.8 ppm (d J=117.8 Hz, each member d J=39.9 Hz, t 13.7 Hz, t 1.7 Hz) 1F, CF$_2$C$\underline{F}$=C.

Anal. Calcd for C$_{11}$F$_{22}$O: C, 23.34; F, 73.84. Found: C, 22.99; F, 73.94.

EXAMPLE 20

2-Trifluoromethoxypentafluoropropene (Perfluoro(allylmethylether))

COF$_2$+CsF+CF$_2$=CFCF$_2$OSO$_2$F→CF$_3$OCF$_2$CF=CF$_2$

A mixture of carbonyl fluoride (18.0 g, 0.27 mol), cesium fluoride (38.0 g, 0.25 mol) and dry diglyme (300 ml) was stirred at −20° C. to −10° C. for 2 hours, then kept at −10° C. or below while perfluoroallyl fluorosulfate (46.0 g, 0.20 mol) was added. The mixture was stirred at −10° C. for 2 hours, at 0° C. for 2 hours, then at 25° C. overnight. The mixture was warmed under a slight vacuum, and the volatile distillate (11 ml of liquid collected at −80° C.) was redistilled through a low temperature still to give 2-trifluoromethoxypropene (3.2 g, 2.0 ml at −80° C., 0.014 mol, 7%) bp 11°–12° C. The structure was established by its spectra: λ$_{max}$ (gas phase) 5.55 (CF=CF$_2$), 8–9 (CF, C—O) and 5.35 μm (weak COF impurity band); $^{19}$F NMR (CCl$_4$), −56.5 (t J=9.2 Hz) 3F, CF$_3$O, −74.6 (d J=25.8 Hz, each member d J=13.6, q J=9.2 Hz, d J=7.1 Hz) 2F, OCF$_2$C=C; −92.2 (d J=53.4 Hz, each member d J=39.2 Hz, t J=7.1 Hz) 1F, cis —CF$_2$CF=C$\underline{F}$, −105.5 (d J=118.0 Hz, each member d J=53.4 Hz, t J=25.8 Hz), 1F, trans-CF$_2$CF=C$\underline{F}$, and −190.9 ppm (d J=118.0 Hz, each member d J=39.2 Hz, t J=13.6 Hz) 1F, CF$_2$C$\underline{F}$=C.

EXAMPLE 21

Perfluoro-6-(2-propenyloxy)hexanoic Acid and Its Methyl Ester

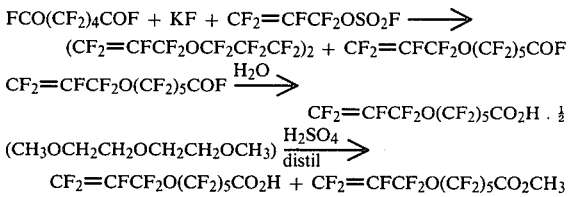

A mixture of potassium fluoride (11.7 g, 0.20 mol), diglyme (250 ml) and octafluoroadipoyl difluoride (PCR 58.8 g, 0.20 mol) was stirred at 0°–5° C. for 30 min. The mixture was kept at 0°–5° C. while perfluoroallyl fluorosulfate (Example 2A, 46.0 g, 0.20 mol) was added dropwise. When the addition was complete, the mixture was stirred at 0°–5° C. for 2 hours, then it was allowed to warm to 25° C. and the stirring was continued for a further 4 hours. Evacuation of the reaction mixture to 35° C. (3 mm Hg) removed 45 ml of liquid. The higher boiling residue was poured in water (1 l.); the lower layer (10 ml) was combined with the volatile fraction from above and treated with a mixture of water (100 ml) and diglyme (20 ml). After the resulting exothermic reaction, the mixture was allowed to cool, and the lower layer was separated and distilled to give perfluoro-1,6-bis(2-propenyloxy)hexane (Example 13, 13.6 g, 0.023 mol, 23%) bp 61° (6 mm Hg) and the 2:1 complex of perfluoro-6-(2-propenyloxy) hexanoic acid with diglyme (Example 13, 52.8 g, 0.109 mol, 54.5%) bp 82°–84° C. (0.8 mm Hg).

The diglyme complex of the higher boiling fraction was distilled from concentrated sulfuric acid (40 ml) to give perfluoro-6-(2-propenyloxy)hexanoic acid containing 12% of its methyl ester. The ester arises from the action of sulfuric acid on the diglyme present in the complex. These products were identified by infrared λ$_{max}$ 2.82 and 3–4 (OH,CH$_3$), 5.58 (CF=CF$_2$), 5.61 (C=O) and 7–10 μm (CF, C—O, CH) and by $^1$H NMR, δ 3.92 (OCH$_3$) and 11.33 ppm (OH) signals in the ratio of 1:7.2; the $^{19}$F NMR spectrum was also in accord with these structures.

EXAMPLE 22

Perfluoro-6-(2-propenyloxy)hexanoic Acid

A reaction was carried out as described in Example 21. The crude reaction mixture was poured into water (750 ml), and the lower layer was washed with water (100 ml). The same two products were obtained as in Example 21 by distillation of the crude lower layer. The fraction bp 45°–53° C. (6 mm Hg) was freed of diglyme by water washing to leave crude perfluoro-1, 6-bis(2-propenyloxy)hexane (9.5 g, 0.016 mol, 16%).

The higher boiling complex of perfluoro-6-(2-propenyloxy)hexanoic acid with diglyme was dissolved in 1,1,2-trichloro-1,2,2-trifluoroethylene (50 ml) and extracted in turn with 50 ml and 25 ml of concentrated sulfuric acid. The organic layer was treated with calcium sulfate, filtered, and distilled to give pure perfluoro-6-(2-propenyloxy)hexanoic acid (42.2 g. 0.0988 mol, 49%) bp 75° C. (1.0 mm Hg). This material was identified by infrared λ$_{max}$ 2.85–4.0 (H-bonded OH), 5.57 (CF=CF$_2$), 5.63 (sh, C=O) and 8–9 μm (CF, C—O), and by its $^1$H and $^{19}$F NMR spectra.

Anal. Calcd. for C$_9$HF$_{15}$O$_3$: C, 24.45; H, 0.23; F, 64.66. Found: C, 24.48; H, 0.45; F, 65.76.

EXAMPLE 23

Perfluoro(4,7-dioxa-6,9-dimethyl-9-propoxy)non-1;-ene

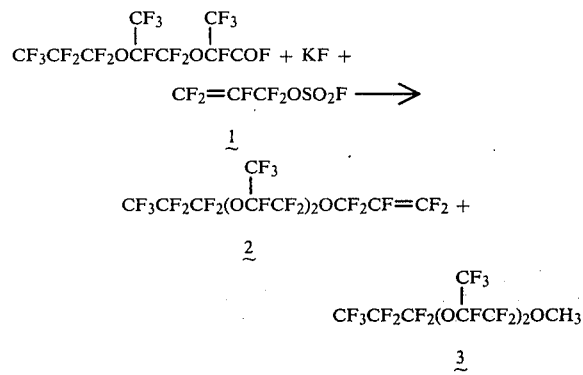

A suspension of 58.1 g (1.0 mol) of flame-dried KF in 1400 ml of dry diglyme was stirred at 25° while 333 g (0.67 mol) of hexafluoropropene oxide trimer was added rapidly. The two-phase system was stirred at 25° for 2 hr, during which time about half of the fluorocarbon layer slowly dissolved. The mixture was stirred at 5°–10° while 230 g (1.0 mol) of 1 was added. The mixture was stirred at 5°–10° for 2.5 hr, then overnight at 25°, and poured into 2 l. of H$_2$O. The aqueous layer was extracted with 100 ml of CFCl$_2$CF$_2$Cl, and the combined organic layers washed with 2 l. of H$_2$O, extracted with 100 ml of conc. H$_2$SO$_4$, clarified with CaSO$_4$, filtered and distilled. Hydrolysis and bubbling were apparent in the water washed. Distillation afforded major fractions of 2 and 3, bp 55°–71° (20 mm) and 140 g of crude CF$_3$CF$_2$CF$_2$OCF(CF$_3$)CF$_2$OCF(CF$_3$-)CO$_2$H, bp mainly 101°–104° (20 mm). Redistillation of combined fractions of 2 and 3 gave 80 g of impure 3, bp 81°–86° (80 mm) and 33.0 g (8%) of 2, bp 94°–95° (80 mm).

For 2, IR (neat): 5.59 (CF=CF$_2$), 7.5–9μ (CF, C—O). NMR: F −72.4 (d of d of t of d, J$_{FF}$ 25.5, 13.2, ∼13, 7.0 Hz, 2F, OCF$_2$C=), =80.9 (m, 8F, 2CF$_3$CF+CFCF$_2$OCF), −82.4 (broad s, 5F, CF$_3$CF$_2$CF$_2$), −84.3 (broad, 2F, CFCF$_2$OCF$_2$), −92.0 (d of d of t of d J$_{FF}$ 52.1, 39.3, 7.0, 3.1 Hz, 1F, cis-CF=CFF), −105.5 (d of d of t, J$_{FF}$ 117.9, 52.1, 25.5 Hz, 1F, trans-CF=CFF), −130.6 (s, 2F, CF$_3$CF$_2$), −146.1 (m, 2F, CF), and −191.1 ppm (d of d of t, J$_{FF}$ 117.9, 39.3, 13.2 Hz, 1F, —CF=CF$_2$).

Anal. Calcd. for C$_{12}$F$_{24}$O$_3$: C, 22.24; F, 70.36. Found: C, 22.50; F, 71.78.

EXAMPLE 24

Perfluoro-6-phenoxy-4-oxa-1-Heptene

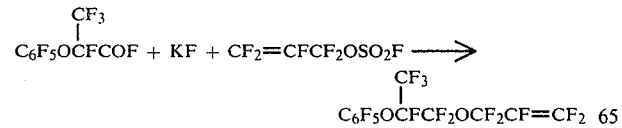

A suspension of 17.4 g (0.30 mol) of flame-dried KF in 500 ml of diglyme was stirred at 5° while 86.1 g (0.26 mol) of perfluoro-2-phenoxypropionyl fluoride prepared by reaction of a metal salt of pentafluorophenol with HFPO) was added dropwise. The mixture was stirred for 30 min at 5°, after which the KF had partially dissolved. Then 69.0 g (0.30 mol) of perfluoroallyl fluorosulfate was added dropwise, and the mixture was stirred at 5°–10° for 3 hr. The cooling bath was removed, and the mixture was stirred overnight. The reaction mixture was then drowned in 2 l. of water, and the lower layer was washed with 1 l., then with 500 ml of water, dried over CaSO$_4$, filtered and distilled to afford 20.8 g (17%) of perfluoro-6-phenoxy-4-oxa-1-heptene, bp 68°–75° (10 mm). A late fraction was analyzed. IR (neat): 5.58 (CF=CF$_2$), 6.57 and 6.80 (arom. C=C, 7.5–9 IR (neat): 5.58 (CF=CF$_2$), 6.57 and 6.80 (arom. C=C), 7.5–9 ‖ (CF, C-O) with a weak peak at 5.64 (—OCF=CFCF$_3$). NMR (CCl$_4$): $^{19}$F −77.8 (d of d of t of d, J$_{FF}$ 25.5, 13.7, ∼13, 7.2 Hz, 2F, OCF$_2$C=), −79.8 (m, 3F, CF$_3$), −83.0 (m, 2F, CF$_2$O), −91.7 (d of d of t, J$_{FF}$ 52.0, 39.2, 7.2 Hz, 1F, cis CF$_2$CF=CFF), −105.1 (d of d of t, J$_{FF}$ 118.0, 52.0, 25.5 Hz, 1F, trans-CF$_2$CF=CFF), −139.9 (t of m, J$_{FF}$ 18.7 Hz, 1F, CF), −150.8 (m, 2F, arom. CF), −156.1 (t, J$_{FF}$ 21.0 Hz, 1F, arom. CF), −162.3 (m, 2F, arom. CF), and −190.6 ppm (d of d of t of t, J$_{FF}$ 118.0, 39.2, 13.7, 1.6 Hz, 1F, CF$_2$CF=). Impurity bands ascribable to the isomer C$_6$F$_5$OCF(CF$_3$)CF$_2$OCF=CFCF$_3$ were also present.

The following examples illustrate the preparation of useful copolymers from the polyfluoroallyloxy comonomers of this invention. The general properties of these copolymers were discussed above.

UTILITY EXAMPLES

Example A

Solution Polymerization of Tetrafluoroethylene with 2-[1-(Pentafluoro-2-propenyloxy)]tetrafluoroethanesulfonyl Fluoride

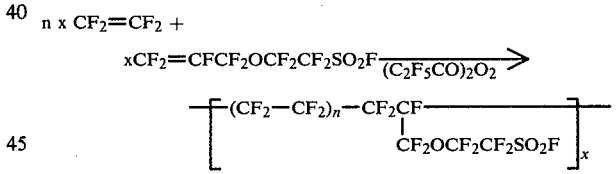

An 80-ml stainless steel-lined tube was charged with a cold mixture (−45° C.) of 1,1,2-trichloro-1,2,2-trifluoroethane (Freon® 113) (10 ml), 8% 1,1,2-trichloro-1,2,2-trifluoroethane solution of pentafluoropropionyl peroxide (3P initiator) (1 ml), and 2-[1-(pentafluoro-2-propenyloxy)]tetrafluoroethanesulfonyl fluoride (Example 7, 17.5 g, 0.053 mol). The tube was closed, cooled to −40° C., evacuated, and charged with tetrafluoroethylene (20 g, 0.20 mol). The tube was warmed to 25° C. and shaken at this temperature for 20 hours. The volatile materials were allowed to evaporate, and the product polymer was evacuated to 0.5 mm Hg. The product was then extracted with 1,1,2-trichloro-1,2,2-trifluoroethane, and dried under vacuum to give the solid white copolymer (16.9 g, 85%): λ$_{max}$ (KBr) 6.79 (So$_2$F) and 12.3 μm (broad) in addition to the usual polytetrafluoroethylene infrared bands. Gravimetric sulfur analysis gave 0.48 and 0.20% S, corresponding to an average of 0.34% S or 3.5 wt. % (1.1 mole %) of polyfluoroallyloxy comonomer corresponding to an equivalent weight of 9400. Equivalent weight is the

Example B

Solution Polymerization of Tetrafluoroethylene with 1-[1-(Pentafluoro-2-propenyloxy)]hexafluoropropane-2-sulfonyl Fluoride

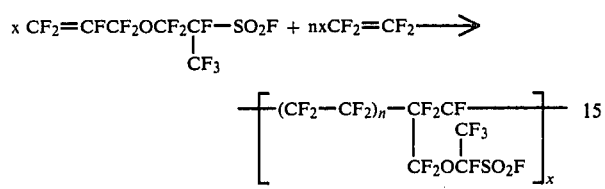

The procedure of Example A was followed with 1,1,2-trichloro-1,2,2-trifluoroethane (10 ml), 8% pentafluoropropionyl peroxide in 1,1,2-trichloro-1,2,2-trifluoroethane (2.0 ml), 1-[1-(pentafluoro-2-propenyloxy)]hexafluoropropane-2-sulfonyl fluoride (Example 9, 17.4 g, 0.046 mol) and tetrafluoroethylene (20 g, 0.20 mol) to give 16.7 g (79%) of copolymer. Analysis by X-ray fluorescence showed 0.49% S present, corresponding to 5.8 wt-% (1.6 mole %) of polyfluoroallyloxy comonomer corresponding to an equivalent weight of 6540. The sample had a mp depression of 11° C. compared to polytetrafluoroethylene by DSC.

Example C

Solution Polymerization of Tetrafluoroethylene with 3-[1-(Pentafluoro-2-propenyloxy)tetrafluoropropionyl Fluoride

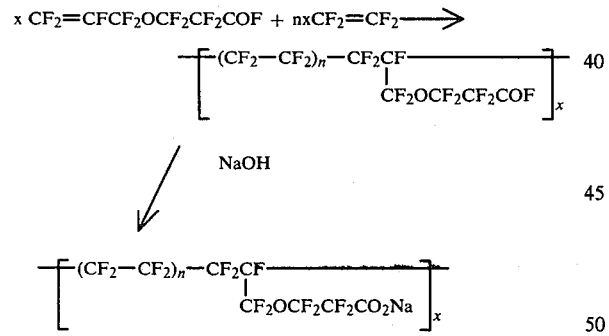

The procedure of Example A was used with 3-[-1(pentafluoro-2-propenyloxy)]tetrafluoropropionyl fluoride (Example 5, 13.3 g, 0.045 mol) in place of 2-[1-(pentafluoro-2-propenyloxy)]-tetrafluoroethanesulfonyl fluoride to give 17.8 g (86%) of copolymer: $\lambda$max (KBr) 5.62 ($CO_2H$, weak) and 9.7 $\mu$m bands in addition to the polytetrafluoroethylene bands; mp depression (DSC) was 14° C. compared to polytetrafluoroethylene; gravimetric analysis showed 3.7 wt % of polyfluoroallyloxy comonomer corresponding to an equivalent weight of 7900.

A sample of the polymer was stirred with a solution of sodium hydroxide in 33% ethanol for 2 days, filtered, and washed with water until the extracts were no longer basic. The resulting polymer, now readily wetted by water, was dried under vacuum. Analysis by atomic absorption spectroscopy showed 0.29% Na, corresponding to 3.7 wt-% (1.3 mole %) of the original comonomer.

Example D

Solution Polymerization of Tetrafluoroethylene with 1-(1,1,1,2,3,3-Hexafluoro-3-chloro-2-propoxy)pentafluoro-2-propene

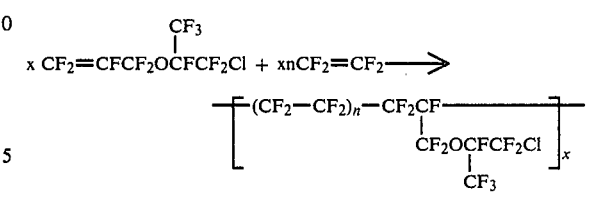

The procedure of Example A was used with 1-(1,1,1,2,3,3-hexafluoro-3-chloro-2-propoxy)pentafluoro-2-propene (Example 2, 14.3 g, 0.043 mol) in place of 2-[1-(pentafluoro-2-propenyloxy)]-tetrafluoroethanesulfonyl fluoride to give 18.3 g (87%) of copolymer: mp depression (DSC) 14° C. compared to polytetrafluoroethylene; gravimetric analysis gave 0.61 and 0.61% Cl, corresponding to 5.7 Wt-% of polyfluoroallyloxy comonomer and an equivalent weight of 5800; more accurate analysis by X-ray fluorescence gave 0.53% Cl corresponding to 5.0 wt-% (1.56 mole %) of polyfluoroallyloxy comonomer. The mp depression of 14° C. compared to polytetrafluoroethylene corresponds to a depression of 1° C. per 0.1 mol % of polyfluoroallyloxy comonomer present. In contrast to this result, the smaller branch in hexafluoropropene gives a mp depression corresponding to about 1° C. per 0.3 mol-% of comonomer in its copolymer with tetrafluoroethylene. This means that the copolymers prepared from the polyfluoroallyloxy comonomers have better molding properties for the same mol-% incorporation of comonomer than those prepared from hexafluoropropene comonomer.

Example E

Solution Polymerization of Tetrafluoroethylene with 2-(1-Pentafluoro-2-propenyloxy)hexafluoropropane-1-sulfonyl Fluoride

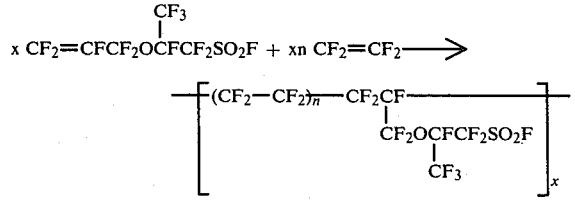

The procedure of Example A was used with 2-(1-pentafluoro-2-propenyloxy)hexafluoropropane-1-sulfonyl fluoride (Example 3, 16.1 g, 0.042 mol) in place of 2-[1-(Pentafluoro-2-propenyloxy)]tetrafluoroethanesulfonyl fluoride to give 18.5 g (88%) of copolymer: mp depression (DSC) 8° C. compared to polytetrafluoroethylene; analysis by X-ray fluorescence showed 0.43% S, corresponding to 5.1 wt-% (1.4 mole %) of polyfluoroallyloxy conomomer and an equivalent weight of 7460.

Example F

Solution Polymerization of Vinylidene Fluoride with 2-[1-(Pentafluoro-2-propenyloxy)]tetrafluoroethanesulfonyl Fluoride

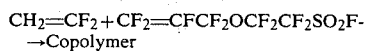
$$CH_2{=}CF_2 + CF_2{=}CFCF_2OCF_2CF_2SO_2F{-} \to \text{Copolymer}$$

The procedure of Example A was used with vinylidene fluoride (20 g, 0.32 mol), 2-[1-(pentafluoro-2-propenyloxy)]tetrafluoroethanesulfonyl fluoride (Example 7, 16.5 g, 0.05 mol), 1,1,2-trichloro-1,2,2-trifluoroethane (10 ml), and 8% 1,1,2-trichloro-1,2,2-trifluoroethane solution of pentafluoropropionyl peroxide (5 ml). The mixture was shaken overnight, the maximum recorded temperature being 31° C. The solid copolymer produced (21.5 g, 60%) contained 46 wt % (14.2 mol %) of polyfluoroallyloxy comonomer with an equivalent weight of 71.9 DSC showed no thermal events between 25° C. and 400° C.

Anal. Calcd for $(CH_2{=}CF_2)6.05 (CF_2{=}CFCF_2OCF_2CF_2SO_2F)$: C, 28.62; H, 1.70; S, 4.7: Found: C, 28.49; H, 1.71; S, 4.46.

Example G

Solution Polymerization of Vinylidene Fluoride with 1-(Heptafluoro-2-propoxy)-1,1,3,3-tetrafluoro-2-chloro-2-propene

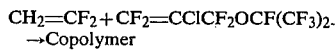
$$CH_2{=}CF_2 + CF_2{=}CClCF_2OCF(CF_3)_2 \to \text{Copolymer}$$

The procedure of Example F was used with 1-heptafluoro-2-propoxy)-1,1,3,3-tetrafluoro-2-chloro-2-propene (Example 1, 10.5 g, 0.032 mol) in place of 2-[1-(pentafluoro-2-propenyloxy)]tetrafluoroethanesulfonyl fluoride to give a solid copolymer (20.6 g, 73%). This material contained 36 wt-% (9.8 mol-%) of polyfluoroallyloxy comonomer with an equivalent weight of 878. DSC confirmed the structure as a copolymer and indicated its stability, because no thermal events were observed in the range 25°–400° C.

Example H

Solution Polymerization of Tetrafluoroethylene with Perfluoro-3-(butoxy)propene

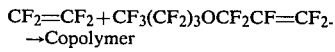
$$CF_2{=}CF_2 + CF_3(CF_2)_3OCF_2CF{=}CF_2 \to \text{Copolymer}$$

The procedure of Example A, when used with perfluoro-3-(butoxy)propene (Example 18, 19.0 g, 0.052 mol), tetrafluoroethylene (20 g, 0.20 mol), 1,1,2-trichloro-1,2,2-trifluoroethane (10 ml) and 8% pentafluoropropionyl peroxide in 1,1,2-trichloro-1,2,2-trifluoroethane (2 ml) gave 18.9 g of solid copolymer. This crude material was chopped in a blender with more solvent, rinsed, and dried to give 16.5 g of copolymer with a mp of 309° C., indicating that it was a true copolymer.

Example I

Solution Polymerization of Tetrafluoroethylene with Perfluoro-1,6-bis(2-propenyloxy)hexane

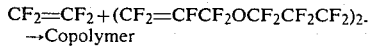
$$CF_2{=}CF_2 + (CF_2{=}CFCF_2OCF_2CF_2CF_2)_2 \to \text{Copolymer}$$

The procedure of Example H was followed, using perfluoro-1,6-bis(2-propenyloxy)hexane (Example 13, 20 g, 0.20 mol) for the polyfluoroallyloxy comonomer. This gave 16.3 g of dry pulverized polymer with $\lambda_{max}$ 5.55 μm (CF=CF$_2$); the remainder of the infrared spectrum resembled that of poly(tetrafluoroethylene). DSC showed a pronounced exotherm Tp 315° C. followed by the endotherm Tp~333° C. and 339° C. on the first heating; the second heating showed no exotherm and a broad endotherm Tp~326° C. Infrared spectra indicated that pyrolytic reactions of pendant pentafluoroallyloxy groups had occurred during the first heating; the broad DSC endotherm near the normally sharp mp of poly(tetrafluoroethylene) indicates that crosslinking had occurred.

Example J

Solution Polymerization of Vinylidene Fluoride and Perfluoro-1,3-bis(2-propenyloxy)propane

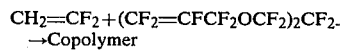
$$CH_2{=}CF_2 + (CF_2{=}CFCF_2OCF_2)_2CF_2 \to \text{Copolymer}$$

A mixture of perfluoro-1,3-bis(2-propenyloxy)propane (Example 17, 5.7 g, 0.013 mol), 1,1,2-trichloro-1,2,2-trifluoroethane (25 ml), and 8% pentafluoropropionyl peroxide in 1,1,2-trichloro-1,2,2-trifluoroethane (5 ml) was held at −40° C. in a stainless steel-lined shaker tube while vinylidene fluoride (20 g, 0.32 mol) was condensed into the tube. The mixture was shaken overnight at room temperature, and the product was isolated as described above. The crude polymer was dried under vacuum, pulverized in a blender with 95% ethanol, filtered and dried to give 24.0 g of solid copolymer. DSC showed an endotherm Tp 124° C., stable to at least 300° C., indicating that a true copolymer had been formed since poly(vinylidene fluoride) has mp 171° C. The insolubility of this product in acetone and the lack of absorption bands in the infrared for pendant CF=CF$_2$ groups indicates that crosslinking had occurred.

Example K

Copolymer of TFE with Methyl Perfluoro-3,6-dioxanon-8-enoate 45 g of methyl perfluoro-3,6-dioxanon-8-enoate and 0.04 g of perfluoropropionyl peroxide were reacted at 50° C. for 4 hr. under a 10 psi pressure of tetrafluoroethylene. Filtration gave a solid which on drying at 50° C. in a vacuum oven weighed 0.71 g. The amount of TFE added was 4 g. Equivalent weight by titration gave 1176; therefore the amount of the ester incorporated in the polymer was 28% and the yield based on TFE was 20%. A transparent film was obtained by heating at 220° C. in a Carver press.

Example L

Dyeable Fluorocarbon Polymers

Samples of the polymers of Examples B and E were treated with aqueous alcoholic ammonia solution for one day at 25° C., filtered, washed with aqueous ethanol and dried under vacuum.

A sample of the polymer of Example C was similarly treated with aqueous alcoholic sodium hydroxide.

The above partly hydrolyzed polymers were immersed in aqueous ethanol solutions of Sevron ® Red GL (Sevron ®) is a line of cationic dyes especially suited for dyeing Orlon ® and other acrylic fibers, having outstanding fastness and brilliance—Du Pont Products Book, January 1975, p. 34) at 25° C. for 1–3 hours, then they are extracted until the extracts no longer contained dye. All three samples dyed well to an orange-red color.

Example M

Wettable Fluorocarbon Polymer

A sample of the polymer of Example C was treated with aqueous alcoholic sodium hydroxide as described in Example L. The resulting fluorocarbon polymer contained carbonyl groups and was wettable with water.

Example N

Emulsion Polymerization of Tetrafluoroethylene with 2-[1-(Pentafluoro-2-propenyloxy)]tetrafluoroethanesulfonyl Fluoride

A stainless steel shaker tube was charged with water (140 ml), 1,1,2-trichloro-1,2,2-trifluoroethane (10 ml), 2-[1-(pentafluoro-2-propenyloxy)]tetrafluoroethanesulfonyl fluoride (Example 7, 6.0 g), potassium perfluorooctanesulfonate (0.16 g), ammonium carbonate (0.50 g) and ammonium persulfate (0.50 g). The mixture was brought to an internal pressure of 200 p.s.i.g. with tetrafluoroethylene and heated to 70° C. Tetrafluoroethylene pressure was maintained at 200 p.s.i.g. for 45 min at 70° C. The polymeric product thus obtained was filtered, washed and dried to give 43.2 g of white solid which contained approximately 1.4 wt % (0.43 mol %) of polyfluoroallyloxy comonomer by infrared analysis. Differential thermal analysis (DTA) showed a crystalline transition at 10° C., a recycle freezing temperature of 293° C. and a recycle melting point of 311° C. from which the polyfluoroallyloxy comonomer content is estimated as 3.5 wt % (1.09 mol %).

Example O

Emulsion Polymerization of Tetrafluoroethylene with 2-[1-(Pentafluoro-2-propenyloxy)]tetrafluoroethanesulfonyl Fluoride

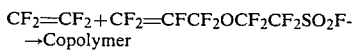

The procedure of Example N was followed using 8.0 g of 2-[1-(pentafluoro-2-propenyloxy)]tetrafluoroethanesulfonyl fluoride, 0.20 g of potassium perfluorooctanesulfonate and tetrafluoroethylene at a pressure of 30 p.s.i.g. at 70° C. for a reaction period of 8 hours. The amounts of the other reagents were not changed. This gave 45 g of solid polymer whose infrared spectrum showed strong $SO_2F$ absorption. DTA showed a crystalline transition at 5° C., a recycle freezing temperature of 282° C., and a recycle melting point of 300° C., corresponding to a polyfluoroallyloxy comonomer content of 5.9 wt % (1.86 mol %).

Example P

Emulsion Polymerization of Tetrafluoroethylene with 2-[1-(Pentafluoro-2-propenyloxy)]tetrafluoroethanesulfonyl Fluoride The procedure of Example N was followed using 10.7 g of 2-[1-pentafluoro-2-propenyloxy)]tetrafluorosulfonyl fluoride, 0.20 g of ammonium persulfate, and tetrafluoroethylene at a pressure of 50 p.s.i.g. at 70° C. for a reaction period of 5 hours. The amounts of other reagents were not changed. This gave 28.6 g of white polymer whose infrared spectrum showed the presence of $SO_2F$ groups corresponding to 3.5 wt % (1.08 mol %) polyfluoroallyloxy comonomer. DTA showed two melting peaks at 290° C. and 317° C., with an estimated conomomer content of 5.5 wt % (1.73 mol %).

Utility Example Q

Copolymerization of Tetrafluoroethylene and 2-[1-(pentafluoro-2-propenyloxy)]tetrafluoroethanesulfonyl Fluoride, and Preparation of Electrically Conductive Films from the Copolymer Product

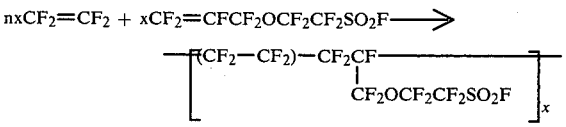

A steel tube charged with 2-[1-pentafluoro-2-propenyloxy)]tetrafluoroethanesulfonyl fluoride (Example 7, 52.8 g) and 6% 1,1,2-trichloro-1,2,2-trifluoroethane solution of pentafluoropropionyl peroxide initiator (0.19 g). The mixture was heated to 40° C. and brought to an internal pressure of 10 psig with tetrafluoroethylene (TFE). TFE pressure was maintained at 10 psig for 6 hours at 40° C. The polymeric product thus obtained was filtered, washed and dried to give a white solid (9.82 g): λmax (KBr) 8.65μ ($SO_2F$) and 8–10 mm (broad) in addition to the usual polytetrafluoroethylene IR bands. The DSC melting point depression was 91° C. compared with polytetrafluoroethylene. Sulfur analysis by x-ray fluorescence gave 2.7% S or 28.0 wt. % (8.5 mol %) of polyfluoroallyloxy comonomer, corresponding to an equivalent weight of 1180.

The product was pressed into a clear 4–5 mil film at 220°–240° C. Four inch diameter film samples were reacted for 1 hour at 90° C. with 13–15% potassium hydroxide solution and dried to give a copolymer of TFE and $CF_2=CFCF_2OCF_2CF_2SO_3^-K^+$. IR spectra showed essentially complete conversion of $-SO_2F$ functions to sulfonate salt.

The four-inch diameter, 4–5 mil film was inserted as the ion exchange membrane in a chlor-alkali electrolysis cell operated at 2.0 amps/in². Cell voltage and current efficiency were measured as a function of cell operating time and sodium hydroxide concentration. The following results were obtained for a 15-day test:

| Day | Sodium Hydroxide Product (%) | Current Efficiency (%) | Cell Voltage (volts) |
| --- | --- | --- | --- |
| 1 | 21.5 | 70.7 | 3.35 |
| 10 | 21.5 | 71.2 | 3.45 |
| 15 | 30.0 | 65.2 | 3.60 |

Utility Example R

Copolymerization of Tetrafluoroethylene and Perfluoro-6-oxanon-8-enoic acid, and Preparation of Electrically Conductive Films from the Copolymer Product

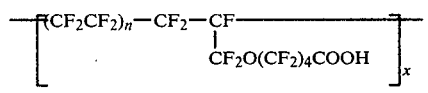

The procedure of Example Q was followed with perfluoro-6-oxanon-8-enoic acid (47.5 g), 8% pentafluoropropionyl peroxide in 1,1,2-trichloro-1,2,2-trifluoroethane (0.05 g), and TFE at 10 psig (40° C.) to give 2.41 g of solid, white copolymer: DSC melting point depression was 157° C. compared with polytetrafluoroethylene. Analysis of carboxyl groups by titration showed 36.8 wt. % (9.3 mol %) of polyfluoroallyloxy comonomer, corresponding to an equivalent weight of 1070.

The copolymer product was pressed into 4–5 mil film and hydrolyzed as described in Example Q. IR spectra showed essentially complete conversion of —COF functions to carboxylate salt, indicating a copolymer of TFE and $CF_2=CFCF_2O(CF_2)_4CO_2^-K^+$.

A four-inch diameter sample of the 4–5 mil film was inserted as the ion-exchange membrane in a chlor-alkali cell operated at 2.0 amps/in$^2$, and the following results were obtained in a 76 day test:

| Day | Sodium Hydroxide Product (%) | Current Efficiency (%) | Cell Voltage (volts) |
|---|---|---|---|
| 1 | 37.1 | 93.3 | 4.02 |
| 20 | 39.2 | 90.9 | 4.60 |
| 35 | 39.4 | 87.7 | 4.25 |
| 50 | 32.9 | 92.0 | 4.11 |
| 76 | 34.6 | 85.8 | 4.67 |

I claim:

1. A polyfluoroallyloxy compound having the formula:

wherein X is —Cl or —F, and $R_F$ is:

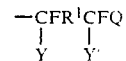

wherein $R^1$ is a carbon-carbon bond or a linear or branched perfluoroalkylene group of 1 to 12 carbon atoms; Q is —CO$_2$H or —CO$_2$R$^4$ where R$^4$ is —CH$_3$ or —C$_2$H$_5$; Y and Y′, independently, are —F or —CF$_3$ providing that only one of Y and Y′ can be —CF$_3$; or

wherein R$^2$ is —CF$_2$CO$_2$H, or —CF$_2$CO$_2$R$^4$ where R$^4$ is defined as above; or

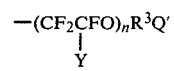

wherein R$^3$ is a linear or branched perfluoroalkylene group of carbon content such that the moiety

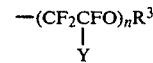

does not exceed 15 carbon atoms; Y is —F or —CF$_3$; n is 1 to 4; and Q′ is defined as for Q above; or

wherein G is —CO$_2$H or —CO$_2$R$^4$ where R$^4$ is —CH$_3$ or —C$_2$H$_5$.

2. The polyfluoroallyloxy compound of claim 1 wherein $R_F$ is

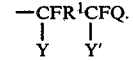

3. The polyfluoroallyloxy compound of claim 2 wherein R$^1$ is a carbon-carbon bond or a linear or branched perfluoroalkylene group of 1 to 8 carbon atoms.

4. The polyfluoroallyloxy compound of claim 3 wherein X is —F.

5. The polyfluoroallyloxy compound of claim 1 wherein $R_F$ is —CF(R$^2$)$_2$.

6. The polyfluoroallyloxy compound of claim 1 wherein $R_F$ is

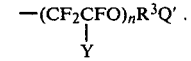

7. The polyfluoroallyloxy compound of claim 6 wherein $R_F$ contains up to 8 carbon atoms.

* * * * *